(12) United States Patent
Nakanishi et al.

(10) Patent No.: US 10,064,692 B2
(45) Date of Patent: Sep. 4, 2018

(54) REMOTE CONTROL APPARATUS AND REMOTE SURGICAL SYSTEM

(71) Applicant: MEDICAROID CORPORATION, Kobe-shi, Hyogo (JP)

(72) Inventors: Tetsuya Nakanishi, Kobe (JP); Kazuki Ishihara, Kobe (JP)

(73) Assignee: MEDICAROID CORPORATION, Kobe-shi (JP)

(*) Notice: Subject to any disclaimer, the term of this patent is extended or adjusted under 35 U.S.C. 154(b) by 0 days.

(21) Appl. No.: 15/372,682

(22) Filed: Dec. 8, 2016

(65) Prior Publication Data

US 2017/0165014 A1 Jun. 15, 2017

(30) Foreign Application Priority Data

Dec. 11, 2015 (JP) ................. 2015-242726

(51) Int. Cl.
*A61B 34/37* (2016.01)
*A61B 34/00* (2016.01)
(Continued)

(52) U.S. Cl.
CPC .......... *A61B 34/37* (2016.02); *A61B 1/00045* (2013.01); *A61B 1/042* (2013.01);
(Continued)

(58) Field of Classification Search
CPC .......... H04N 5/4403; H04N 21/42207; H04N 21/42224; H04N 21/42204;
(Continued)

(56) References Cited

U.S. PATENT DOCUMENTS 6,436,107 B1 8/2002 Wang et al.
8,170,716 B2 * 5/2012 Coste-Maniere ...... B25J 9/1671
128/897

(Continued)

FOREIGN PATENT DOCUMENTS

EP 2092892 A1 8/2009
JP 2002-537884 A 11/2002
(Continued)

OTHER PUBLICATIONS

Claire C. Gordon et al., 1988 Anthropometric Survey of U.S. Army Personnel: Methods and Summary Statistics, Technical Report, Sep. 1989, Natick/TR-89/044, Anthropology Research Project, Inc. Yellow Springs, Ohio 45387 (Table of Contents provided), Full text available at "http://www.dtic.mil/dtic/tr/fulltext/u2/a209600.pdf".

(Continued)

*Primary Examiner* — Mark Blouin
(74) *Attorney, Agent, or Firm* — Metrolexis Law Group, PLLC

(57) ABSTRACT

A remote control apparatus may transmit, to a surgical manipulator, a movement type instruction to be executed by the surgical manipulator. The apparatus may comprise a movable operating handle positioned within an operation area. The movable operating handle may receive the movement type instruction. The apparatus may further comprise a support mechanism that supports and transforms the operating handle between a first posture in which the operating handle at a center position of the operation area is positioned and held at a first vertical position located at a height of 85 centimeters or more from a floor surface where the remote control apparatus is placed, and a second posture in which the operating handle is shifted down by 48 centimeters or more from the first vertical position to a second vertical position at which the operating handle at the center position of the operation area is positioned and held.

20 Claims, 17 Drawing Sheets

(51) Int. Cl.
*A61B 1/00* (2006.01)
*A61B 1/04* (2006.01)

(52) U.S. Cl.
CPC .............. *A61B 34/25* (2016.02); *A61B 34/74* (2016.02); *A61B 2034/258* (2016.02); *A61B 2034/742* (2016.02)

(58) Field of Classification Search
CPC ....... H04N 21/42208; H04N 21/42209; H04N 2005/4435
USPC ...................................................... 340/12.54
See application file for complete search history.

(56) References Cited

U.S. PATENT DOCUMENTS

| | | | | |
|---|---|---|---|---|
| 8,219,178 B2* | 7/2012 | Smith | ...................... | A61B 5/06 600/411 |
| 8,463,439 B2* | 6/2013 | Blumenkranz | ........ | A61B 34/30 385/33 |
| 8,808,369 B2* | 8/2014 | Suri | ...................... | A61F 2/2418 623/2.1 |
| 9,266,239 B2* | 2/2016 | Miller | .................... | B25J 9/1676 |
| 9,474,580 B2* | 10/2016 | Hannaford | .............. | G06F 3/011 |
| 9,492,240 B2* | 11/2016 | Itkowitz | ................. | A61B 34/37 |
| 9,610,689 B2* | 4/2017 | Swarup | .................. | B25J 9/1643 |
| 9,636,177 B2* | 5/2017 | Mohr | ..................... | A61B 18/24 |
| 9,645,785 B1* | 5/2017 | Hannaford | ............ | G06F 3/1454 |
| 9,696,700 B2* | 7/2017 | Beira | ................ | A61B 17/00234 |
| 9,713,499 B2* | 7/2017 | Bar | ......................... | A61B 34/30 |
| 9,786,203 B2* | 10/2017 | Wang | ..................... | G09B 23/28 |
| 2003/0220564 A1 | 11/2003 | Wilkins et al. | | |
| 2009/0192519 A1 | 7/2009 | Omori | | |
| 2010/0094130 A1 | 4/2010 | Ninomiya et al. | | |
| 2010/0225209 A1 | 9/2010 | Goldberg et al. | | |
| 2010/0331859 A1 | 12/2010 | Omori | | |
| 2011/0087238 A1 | 4/2011 | Wang et al. | | |
| 2014/0195010 A1 | 7/2014 | Beira et al. | | |
| 2015/0157410 A1 | 6/2015 | Kilroy et al. | | |

FOREIGN PATENT DOCUMENTS

| | | |
|---|---|---|
| JP | 2003225198 A | 8/2003 |
| JP | 2005-526567 A | 9/2005 |
| JP | 2005-342056 A | 12/2005 |
| JP | 2008-126015 A | 6/2008 |
| JP | 2009178230 A | 8/2009 |
| WO | 2015143073 A1 | 9/2015 |
| WO | 2016/137527 A1 | 9/2016 |
| WO | 2016/171757 A1 | 10/2016 |

OTHER PUBLICATIONS

Japanese Industrial Standards (JIS), Ergonomic design of control centres Part 4 : Layout and dimensions of workstations, JIS Z8503-4: 2006 (ISO 11064-4: 2004), 17 pages, Japan.

* cited by examiner

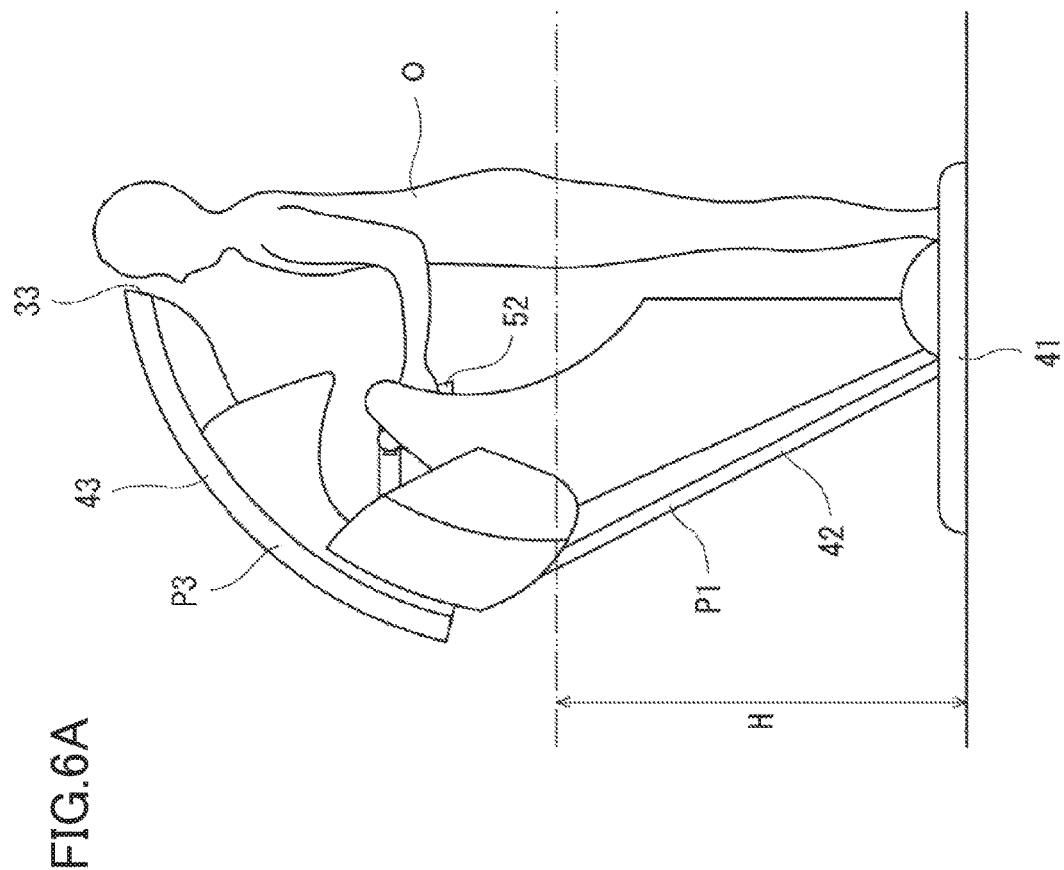

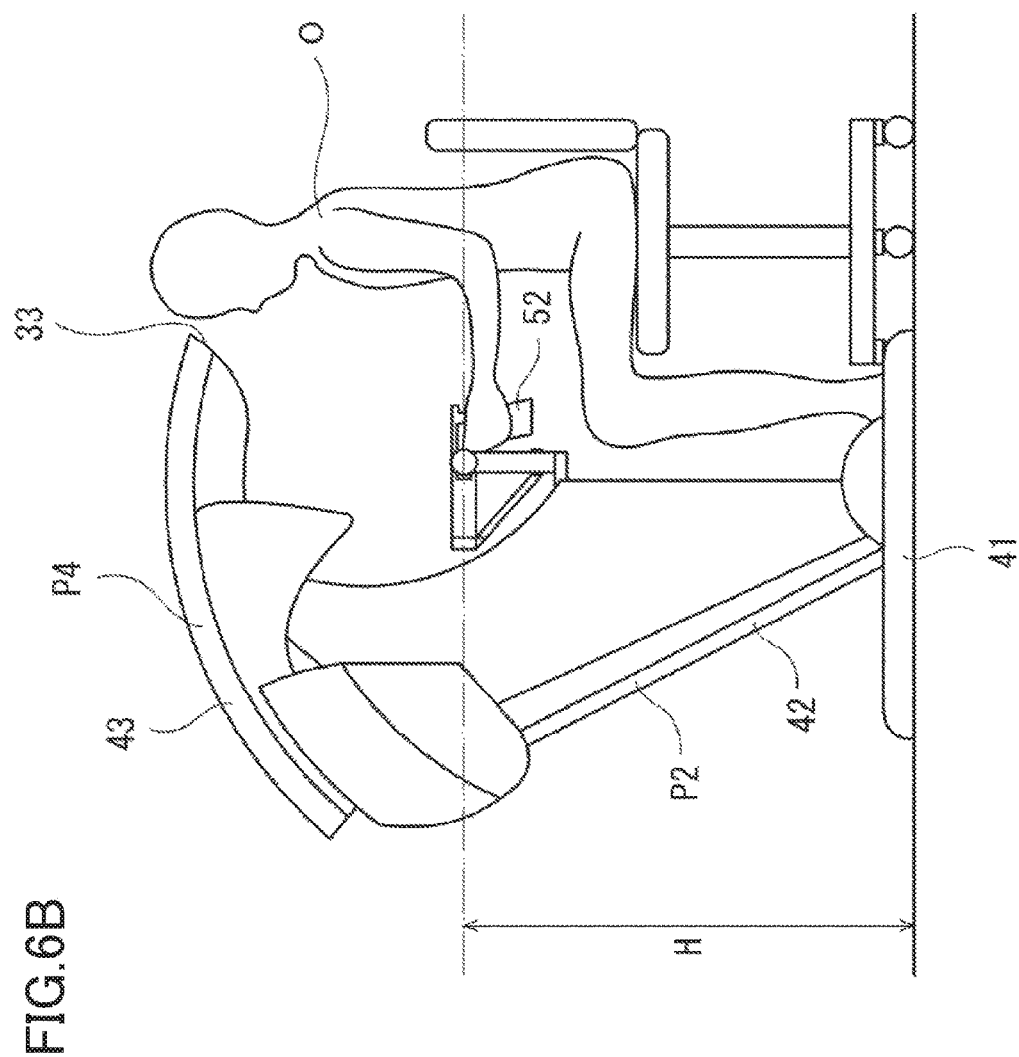

REMOTE CONTROL APPARATUS AND REMOTE SURGICAL SYSTEM

CROSS-REFERENCE TO RELATED APPLICATION

This application claims priority to Japanese Patent Application No. 2015-242726 filed on Dec. 11, 2015, the entire contents of which is incorporated herein by reference.

TECHNICAL FIELD

One or more embodiments relate to a remote control apparatus and a remote surgical system.

BACKGROUND ART

Minimally invasive surgical systems having a handle for operating a surgical manipulator have been known.

For example, the system disclosed in U.S. Patent Application Publication No. 2011/0087238 (Patent Document 1) includes a cabinet having handles used by an operator in a standing position. The operator operates the robot arms by operating the handles while in the standing position.

On the other hand, the system disclosed in U.S. Patent Application Publication No. 2014/0195010 (Patent Document 2), for example, is provided with handles used by an operator in a seated position. The operator operates an end effector by using the handles while in the seated position.

SUMMARY

However, systems, such as those disclosed in Patent Document 1 and apparatuses, such as the apparatus disclosed in Patent Document 2, may require operators to use the handles either in the standing position or in the seated position, and do not allow operators to take a particular desired position.

A remote control apparatus according to one or more embodiments may be directed to a remote control apparatus which transmits, to a surgical manipulator, a movement type instruction to be executed by the surgical manipulator. A remote control apparatus in accordance with one or more embodiments may include: an operating handle configured to be movable within a predetermined operation area, and configured to be used to input the movement type instruction to be executed by the surgical manipulator; and a support mechanism which supports the operating handle.

The support mechanism may be configured to be capable of transforming or translating between a first posture in which the operating handle at a center position of the operation area is positioned and held at a first vertical position located at a height of 85 centimeters or more from a floor surface where the remote control apparatus is placed, and a second posture in which the operating handle is shifted down by 48 centimeters or more from the first vertical position to a second vertical position at which the operating handle at the center position of the operation area is positioned and held.

BRIEF DESCRIPTION OF THE DRAWINGS

FIG. 6A is a diagram illustrating a side view of an example configuration of a remote control apparatus in a standing position posture in a remote surgical system in accordance with one or more embodiments.

FIG. 6B is a diagram illustrating a side view of an example configuration of a remote control apparatus in a seated position posture in a remote surgical system in accordance with one or more embodiments.

DETAILED DESCRIPTION

Figure 1:
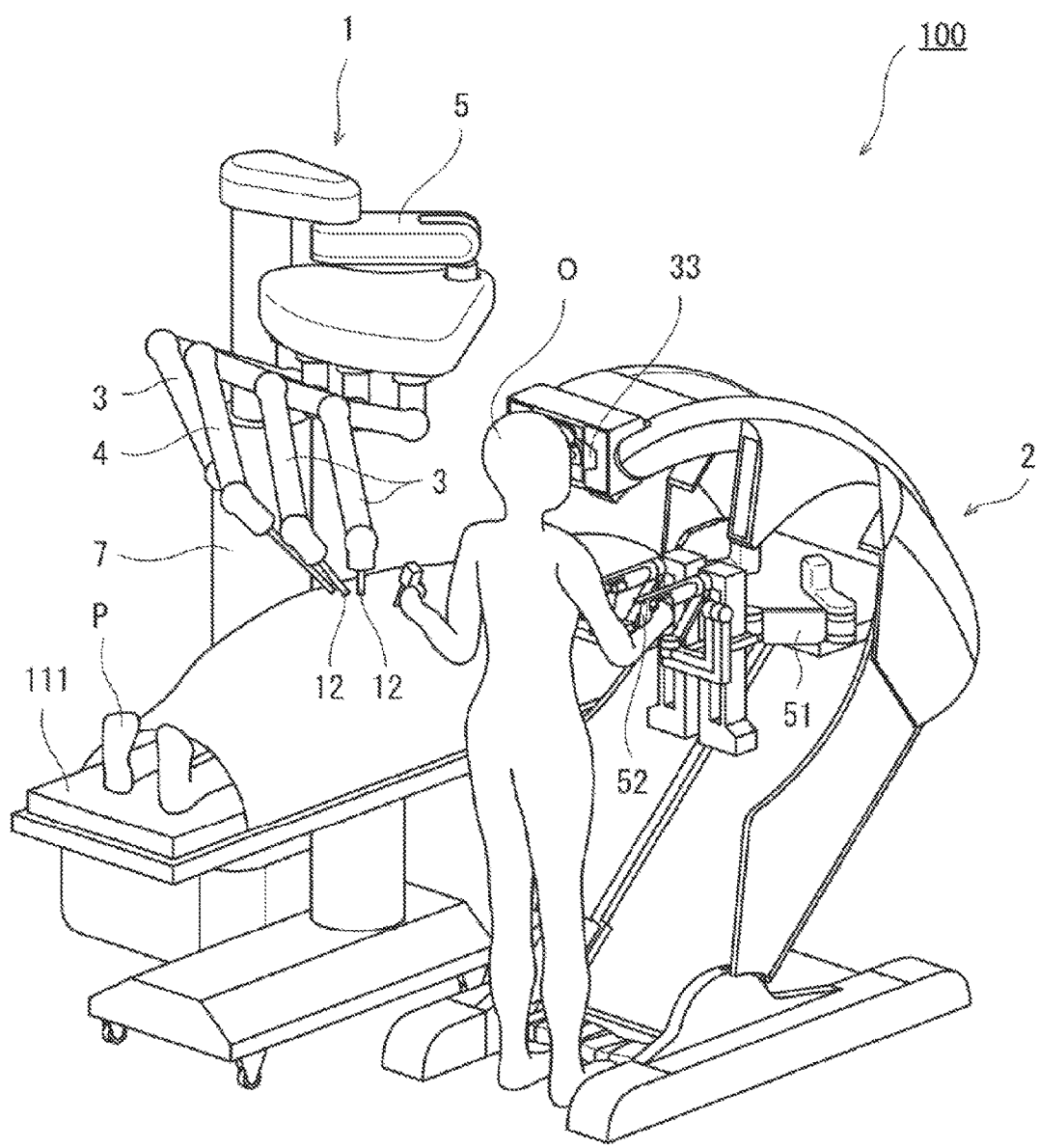
FIG. 1 is a diagram illustrating a perspective view of an example configuration of a remote surgical system according to one or more embodiments.

A remote control apparatus according to one or more embodiments, may transmit, to a surgical manipulator, a movement type instruction to be executed by the surgical manipulator. The remote control apparatus may comprise an operating handle configured to be movable within a predetermined operation area, and to be used to input the movement type instruction to be executed by the surgical manipulator; and a support mechanism that supports the operating handle. The support mechanism may be configured to transform or to be capable of transforming between a first posture in which the operating handle at a center position of the operation area is positioned and held at a first vertical position located at a height of 85 centimeters or more from a floor surface where the remote control apparatus is placed, and a second posture in which the operating handle is shifted down by 48 centimeters or more from the first vertical position to a second vertical position at which the operating handle at the center position of the operation area is positioned and held.

In the disclosed configuration or configurations, the remote control apparatus in the first posture may allow the operator to operate the remote control apparatus while in the stand-up position. Further, the remote control apparatus in the second posture allows the operator to operate the remote control apparatus while in the sitting-on-chair position. Providing the first posture and the second posture may allow an operator to change a position between a standing position and a seated position while operating the remote control apparatus, and to operate the remote control apparatus while in a position that the operator desires, prefers or likes.

In the first posture of the remote control apparatus, the support mechanism may hold the operating handle so that the operating handle at the center position of the operation area can be positioned at the first vertical position located at a height of 99 centimeters or more from the floor surface where the remote control apparatus is placed.

In the disclosed configuration, e.g. having the first vertical position, a large number of operators having different body sizes can operate the operating handle comfortably while in the standing position.

In the second posture of the remote control apparatus, the support mechanism may shift the operating handle down by 50 centimeters or more from the first vertical position to the second vertical position at which the operating handle at the center position of the operation area is positioned and held.

In the disclosed configuration, e.g., having the first vertical position and the second vertical position, a large number of operators having different body sizes can operate the operating handle comfortably while in the standing position or in the seated position.

A remote control apparatus, according to one or more additional embodiments may transmit, to a surgical manipulator, a movement type instruction to be executed by the surgical manipulator. The remote control apparatus may comprise: an operating handle configured to be movable within a predetermined operation area, and configured to be used to input the movement type instruction to be executed by the surgical manipulator; and a support mechanism that supports the operating handle. The support mechanism may be configured to transform or to be capable of transforming between a first posture in which the operating handle is held such that the operation area of the operating handle is included in a clean zone that is set at and above a predetermined height from a floor surface where the remote control apparatus is placed, and a second posture in which the operating handle is held such that at least part of the operation area of the operating handle is located in a zone below the clean zone.

In the disclosed configuration, e.g., having the first and second postures in which the operation area of the operating handle is included or located relevant to the clean zone, the remote control apparatus may transform between the first posture and the second posture according to how a surgery is carried out. That is, the remote control apparatus in the first posture may prevent the contamination of the operating handle and the hands of the operator allowing the operator to switch from the operating handle to a surgical instrument as necessary, and to continue the surgery without a cleaning procedure. Further, the transformation of the remote control apparatus between the first posture and the second posture allows the operator to change position while operating the remote control apparatus, and thus to operate the remote control apparatus while in a position that the operator desires, prefers or likes.

In accordance with one or more embodiments, the clean zone may be set at and above 70 centimeters from the floor surface.

In a disclosed configuration in which the clean zone is set relative to the floor surface, contamination of the operating handle and the hands of the operator may be advantageously prevented.

In the second posture of the remote control apparatus, a vertical position of a lower limit of the operation area of the operating handle may be at least 48 centimeters lower than a vertical position of a lower limit of the operation area of the operating handle in the first posture of the remote control apparatus.

In the disclosed configuration of the first and the second postures, a large number of operators having different body sizes can operate the operating handle comfortably while in the standing position or in the seated position.

A remote control apparatus according to one or more additional embodiments, may transmit, to a surgical manipulator, a movement type instruction to be executed by the surgical manipulator. The remote control apparatus may comprise a support mechanism that comprises: a support base; a lower support having a proximal end attached to the support base via a first axis extending in a horizontal direction, and that is able to pivot about the first axis; and an upper support having a proximal end attached to a distal end of the lower support via a second axis extending in the horizontal direction, and that is able to pivot about the second axis; and an operating handle attached to the lower support so as to be located behind the lower support, and used to input the movement type instruction to be executed by the surgical manipulator.

In the above disclosed configuration, the vertical positions of the operating handle and the display section can be changed by the pivotal movements of the lower support and the upper support allowing the operator to change position while operating the remote control apparatus. As a result, the operator can operate the remote control apparatus while in a position that the operator desires, prefers or likes.

In accordance with one or more of embodiments, such as those disclosed above, the lower support may be configured so as to be able to pivot between a standing angle position where the lower support extends obliquely upward and forward from the support base, and a leaning angle position to which the lower support is rotated forward from the standing angle position. The upper support may be able to pivot between a wide angle position where the upper support extends obliquely upward and backward from the distal end of the lower support at the standing angle position, and a narrow angle position where the upper support forms a smaller angle with respect to the lower support than when the upper support is positioned at the wide angle position.

In the above-disclosed configuration, the vertical positions of the operating handle and the display section can be changed by the pivotal movement of the lower support between the standing angle position and the leaning angle position, and by the pivotal movement of the upper support between the wide angle position and the narrow angle position, allowing the operator to change position while operating the remote control apparatus. As a result, the operator can operate the remote control apparatus while in a position that the operator desires, prefers or likes.

In accordance with one or more embodiments, the first axis and the second axis may be approximately parallel to each other.

In a configuration in which the first axis and the second axis are approximately parallel, the remote control apparatus can be advantageously configured.

The operating handle may be configured to be able to move within a predetermined operation area. In a first posture of the remote control apparatus, in which the lower support is positioned at the standing angle position and the upper support is positioned at the wide angle position, the support mechanism may position and hold the operating handle at a center position of the operation area at a first vertical position located at a height of 85 centimeters or more from a floor surface where the remote control apparatus is placed. In a second posture of the remote control apparatus, in which the lower support is positioned at the leaning angle position and the upper support is positioned at the narrow angle position, the support mechanism may position and hold the operating handle at the center position of the operation area at a second vertical position located at least 48 centimeters lower than the first vertical position.

In the above disclosed configuration, the remote control apparatus in the first posture allows the operator to operate the remote control apparatus while in the stand-up position. Further, the remote control apparatus in the second posture allows the operator to operate the remote control apparatus while in the sitting-on-chair position. Providing the first posture and the second posture allows the operator to change position while operating the remote control apparatus, and to operate the remote control apparatus while in a position that the operator desires, prefers or likes.

The operating handle may be configured to be able to move within a predetermined operation area. In a first posture of the remote control apparatus, in which the lower support is positioned at the standing angle position and the upper support is positioned at the wide angle position, the support mechanism may hold the operating handle such that the operation area of the operating handle is included in a clean zone that is set at and above a predetermined height from a floor surface where the remote control apparatus is placed. In a second posture of the remote control apparatus, in which the lower support is positioned at the leaning angle position and the upper support is positioned at the narrow angle position, the support mechanism may hold the operating handle such that at least part of the operation area of the operating handle is located in a zone below the clean zone.

In the above disclosed configuration, the remote control apparatus in the first posture can prevent the contamination of the operating handle and the hands of the operator during a surgery in which a treatment using a surgical manipulator and a treatment manually provided by the operator are alternately conducted. Preventing contamination therefore allows the operator to switch from the operating handle to a surgical instrument as necessary, and continue the surgery without a cleaning procedure.

The clean zone may be set at and above 70 centimeters from the floor surface.

In the above-disclosed configuration, contamination of the operating handle and the hands of the operator can be advantageously prevented.

A remote control apparatus according to one or more additional embodiments may transmit, to a surgical manipulator, a movement type instruction to be executed by the surgical manipulator, and which receives an image taken by an endoscope camera probe. The remote control apparatus may comprise: an operating handle used to input the movement type instruction to be executed by the surgical manipulator; a display section which displays the image taken by the endoscope camera probe; and a support mechanism which supports the operating handle and the display section. The remote control apparatus may be configured to transform or to be able to transform between a first posture suitable for an operator in a standing position to operate the remote control apparatus, and a second posture suitable for an operator in a seated position to operate the remote control apparatus. The support mechanism supports the display section such that a relative position of the display section with respect to the operating handle is changeable in each of the first and second postures.

In the above-disclosed configuration, the position of the display section can be changed according to whether the operator is in the standing position or the seated position.

In accordance with one or more embodiments, the display section may be attached to the support mechanism so as to be rotatable about an axis extending in a horizontal direction.

In the above-disclosed configuration, the position of the display section can be changed more advantageously according to whether the operator is in the standing position or the seated position.

A remote control apparatus according to one or more additional embodiments may transmit, to a surgical manipulator, a movement type instruction to be executed by the surgical manipulator, and which receives an image taken by an endoscope camera probe. The remote control apparatus may comprise a display device which receives the image taken by the endoscope camera probe and displays the received image. The remote control apparatus may be configured to transform or to be able to transform between a first posture suitable for an operator in a standing position to operate the remote control apparatus, and a second posture suitable for an operator in a seated position to operate the remote control apparatus. The display device may be provided at a height suitable for the operator to view the image on the display device in the first posture, and an additional display device other than the display device may be used in the second posture.

In the above disclosed configuration, the operator operating the remote control apparatus can use the operating handle while watching a display device and an additional display device instead of the display section. Thus, if the operator feels tired during a surgery, from watching the display device for a long time, the operator can switch to watching the additional display device instead of the display device in the surgery, which may reduce the fatigue of the operator.

In accordance with one or more embodiments, the additional display device may be attached such that an angle thereof is adjustable.

In the above-disclosed configuration, the remote control apparatus can be configured more advantageously.

A remote surgical system according to one or more embodiments, may comprise: the above described remote control apparatus; and the above described additional display device as an external device of the remote control apparatus.

In the above-disclosed configuration, the operator operating the remote control apparatus of the remote surgical system can use the operating handle while watching a display device and an additional display device instead of the display section. Thus, if the operator feels tired during a surgery, from watching the display device for a long time, the operator can switch to watching the additional display device instead of the display device in the surgery, which can reduce the fatigue of the operator.

A remote control apparatus according to one or more additional embodiments, may transmit, to a surgical manipulator, a movement type instruction to be executed by the surgical manipulator. The remote control apparatus may comprise an operating handle configured to be movable within a predetermined operation area, and used to input the movement type instruction to be executed by the surgical manipulator. The remote control apparatus may be configured to transform or to be able to transform between a first posture suitable for an operator in a standing position to operate the remote control apparatus, and a second posture suitable for an operator in a seated position to operate the remote control apparatus. While the postures are changed between the first posture and the second posture, either operation by the operating handle or transmission of the movement type instruction is invalidated.

In the above-disclosed configuration, the movement type instruction to be executed by a surgical manipulator can be prevented from being transmitted to the surgical manipulator, and hence be prevented from activating the surgical manipulator unintentionally, when the remote control apparatus transforms between the first posture and the second posture.

A remote surgical system according to one or more additional embodiments, may comprise a remote control apparatus which transmits, to a surgical manipulator, a movement type instruction to be executed by the surgical manipulator, and a patient-side surgery apparatus which includes the surgical manipulator and moves the surgical manipulator in response to the movement type instruction. The remote control apparatus may comprise: an operating handle configured to be movable within a predetermined operation area, and used to input the movement type instruction to be executed by the surgical manipulator; and a support mechanism which supports the operating handle. The support mechanism may be configured to transform or to be able to transform between a first posture in which the operating handle is held such that the operating handle at a center position of the operation area is positioned at a first vertical position located at a height of 85 centimeters or more from a floor surface where the remote control apparatus is placed, and a second posture in which the operating handle is shifted down by 48 centimeters or more from the first vertical position to a second vertical position at which the operating handle at the center position of the operation area is positioned and held.

In the above-disclosed configuration, the remote control apparatus in the first posture allows the operator to operate the remote control apparatus while in the stand-up position. Further, the remote control apparatus in the second posture allows the operator to operate the remote control apparatus while in the sitting-on-chair position. Providing the first posture and the second posture allows the operator to change position between the standing position and the seated position while operating the remote control apparatus, and to operate the remote control apparatus while in a position the operator desires, prefers or likes.

One or more embodiments of a remote control apparatus and a remote surgical system are described below with reference to the drawings. Note that the following embodiments are not intended to be limiting in scope. Also, in the following description, the same reference characters will be used to designate the same or equivalent elements throughout the drawings, and redundant explanations of the same or equivalent elements will be omitted herein.

In an operating room, a cleaning procedure is carried out to prevent surgery incisions and medical equipment from being infected and contaminated with pathogenic bacteria or foreign substances. A clean zone and a contaminated zone, which is a zone other than the clean zone, are defined in this cleaning procedure. A zone covering a range with a certain height from the floor surface where foreign substances, e.g., dust or dirt, are highly likely to be present is generally treated as the contaminated zone, and excluded from the clean zone. In general, the contaminated zone covers a range up to a height of 70 centimeters (cm) from the floor surface.

Surgery team members, including an operator, take good care so that only a disinfected object is placed in the clean zone during the surgery, and sterilize the object placed in the contaminated zone when it needs to be moved to the clean zone. Similarly, if the surgery team members, including the operator, have put their hands in the contaminated zone, they sterilize their hands before they directly touch an object placed in the clean zone. One or more embodiments described below are related to such an observation about the cleaning procedure.

First Embodiment

FIG. 1 is a diagram illustrating a perspective view of an example configuration of a remote surgical system 100 according to one or more embodiments.

Example Configuration of Remote Surgical System

As illustrated in FIG. 1, the remote surgical system 100 may be configured to perform surgery, such as a minimally invasive surgery. The remote surgical system 100 may include a patient-side surgery apparatus 1 and a remote control apparatus 2. The remote control apparatus 2 receives, from an operator O (e.g., a surgeon), a movement type instruction to be executed by the patient-side surgery apparatus 1, and transmits the movement type instruction to the patient-side surgery apparatus 1. The patient-side surgery apparatus 1 then handles surgical instruments and other tools in response to the movement type instruction transmitted from the remote control apparatus 2. The remote surgical system 100 may perform a minimally invasive surgery by remotely operating instrument arms 3 and other tools from the remote control apparatus 2.

Example Configuration of Patient-Side Surgery Apparatus

The patient-side surgery apparatus 1 may constitutes an interface between the remote surgical system 100 and a patient P. The patient-side surgery apparatus 1 may be arranged beside a surgical table 111 on which the patient lies.

The patient-side surgery apparatus 1 may include one or more instrument arms 3, one or more camera arms 4, and a positioner 5, which supports and positions the respective instrument arms 3 and camera arms 4. The instrument arms 3 and the camera arms 4 may serve as a surgical manipulator. The positioner 5 is supported on a base 7 placed on the floor of the operating room. In a general example, two or more instrument arms 3 and one camera arm 4 may be provided.

The instrument arms 3 may each be configured such that a holder at the tip thereof holds an instrument 12. The instrument 12 may be configured as a long shaft having an end effector at the tip end. Examples of the end effector include a forceps, a high-frequency knife, and a snare wire, but are not limited thereto, and may include various types of treatment tools. In a surgery using the remote surgical system 100, each of the instrument arms 3 may be introduced into the body of the patient P through a sleeve (e.g., a cannula sleeve or the like) retained on the body surface of the patient P, so that the end effector of the instrument 12 is positioned close to a surgical site.

The camera arm 4 has an endoscope camera probe 13 (see FIG. 4) attached to the tip end thereof. The endoscope camera probe 13 takes images of the surgical site in the body of the patient P. The images taken are output to the remote control apparatus 2. In one or more embodiments, the endoscope camera probe 13 is a 3D endoscope capable of taking three-dimensional images. In a surgery using the remote surgical system 100, the camera arm 4 is introduced into the body of the patient P through a trocar retained on the body surface of the patient P, so that the endoscope camera probe 13 is positioned close to the surgical site.

Example Configuration of Remote Control Apparatus

Figure 4:
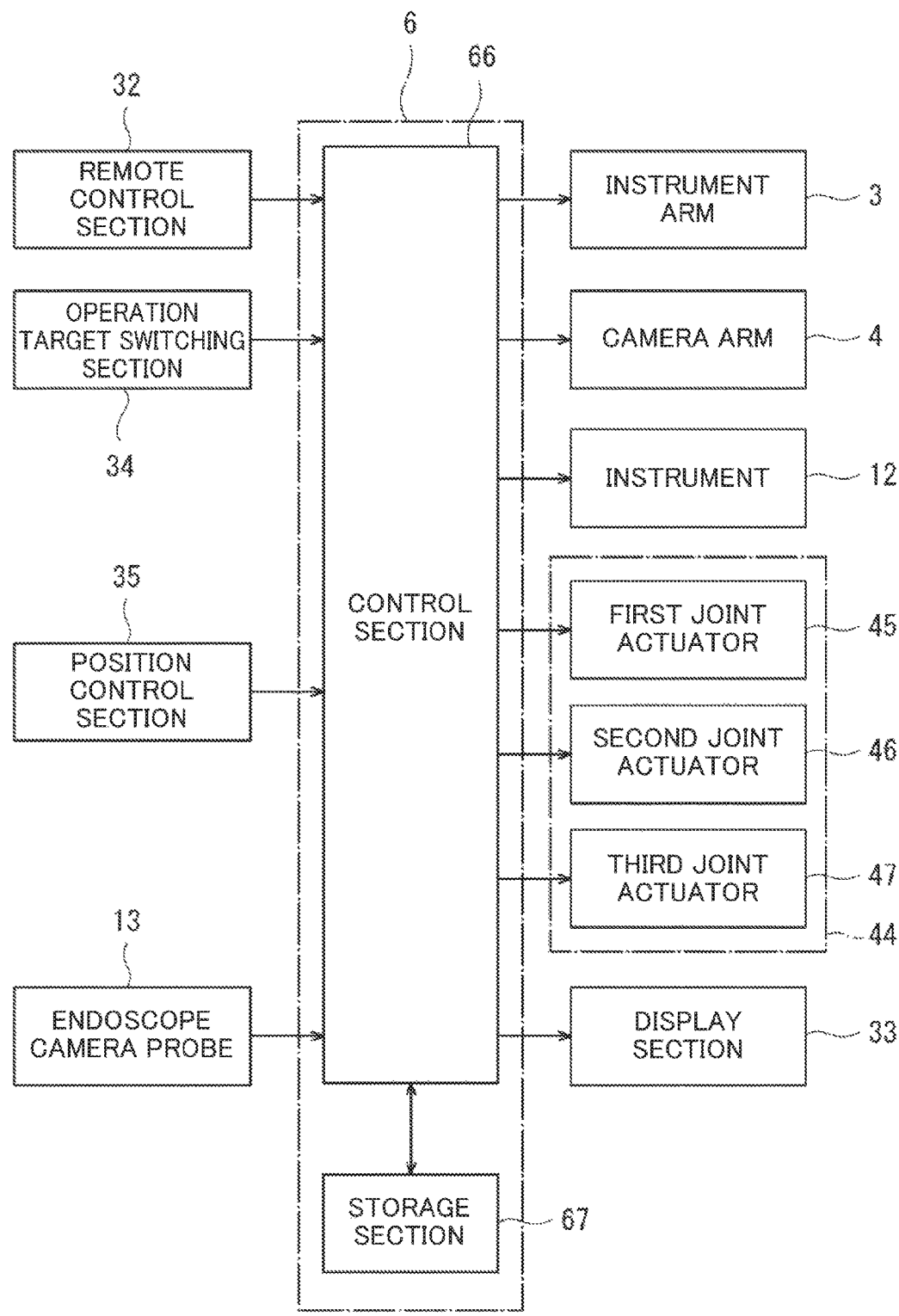
FIG. 4 is a block diagram illustrating an example configuration of a control system of a remote surgical system in accordance with one or more embodiments.

The remote control apparatus 2 constitutes an interface between the remote surgical system 100 and the operator O, and serves as a device through which the operator O operates the respective instrument arms 3, the instruments 12, the camera arm 4, and the endoscope camera probe 13 (see e.g., FIG. 4). That is, the remote control apparatus 2 is configured to be able to transmit, to the patient-side surgery apparatus 1, the movement type instruction that has been input by the operator O and that should be executed by the instrument arms 3, the instruments 12, the camera arm 4, and the endoscope camera probe 13. The remote control apparatus 2 is also configured to be able to display the images taken by the endoscope camera probe 13. The remote control apparatus 2 is installed, for example, beside the surgical table 111, or may also be installed in a separate room.

As used herein, the term "movement type" may refer to a movement, translation or transformation to be performed by the instrument arms 3, which may include, for example, shifting and positioning of the instrument 12. The positioning may include determination of the orientation of the instrument 12.

The movement type to be performed by the instrument 12 is a type of movement executed by the function of the instrument 12. For example, if the instrument 12 is a forceps, the movement type to be performed by the instrument 12 may be holding something, and releasing something. If the instrument 12 is a high-frequency knife, the movement type to be performed by the instrument 12 may be vibration of the high-frequency knife, specifically, by way of a current supply to the high-frequency knife. If the instrument 12 is a snare wire, the movement type to be performed by the instrument 12 may be tightening, and releasing from the tightening, or may further include a movement of burning off a target site of the surgery, using the snare wire to which an electric current is supplied.

Examples of the movement type to be performed by the camera arm 4 include shifting and positioning of the endoscope camera probe 13. The positioning may include determination of the orientation of the endoscope camera probe 13.

Examples of the movement type to be performed by the endoscope camera probe 13 further include setting of zoom magnification of the endoscope camera probe 13.

In the following description, for the sake of convenience, the forward and backward directions may include directions as viewed from the operator O who is operating the remote control apparatus 2, and will be simply called "front" or "fore" and "back" or "aft," respectively, and the leftward and rightward directions may include directions as viewed from the operator O who is operating the remote control apparatus 2 will be simply called "left" and "right," respectively.

The remote control apparatus 2 transmits the movement type instruction to be executed by the patient-side surgery apparatus 1 to the instrument arms 3. The remote control apparatus 2 also receives the images taken by the endoscope camera probe 13.

Figure 2:
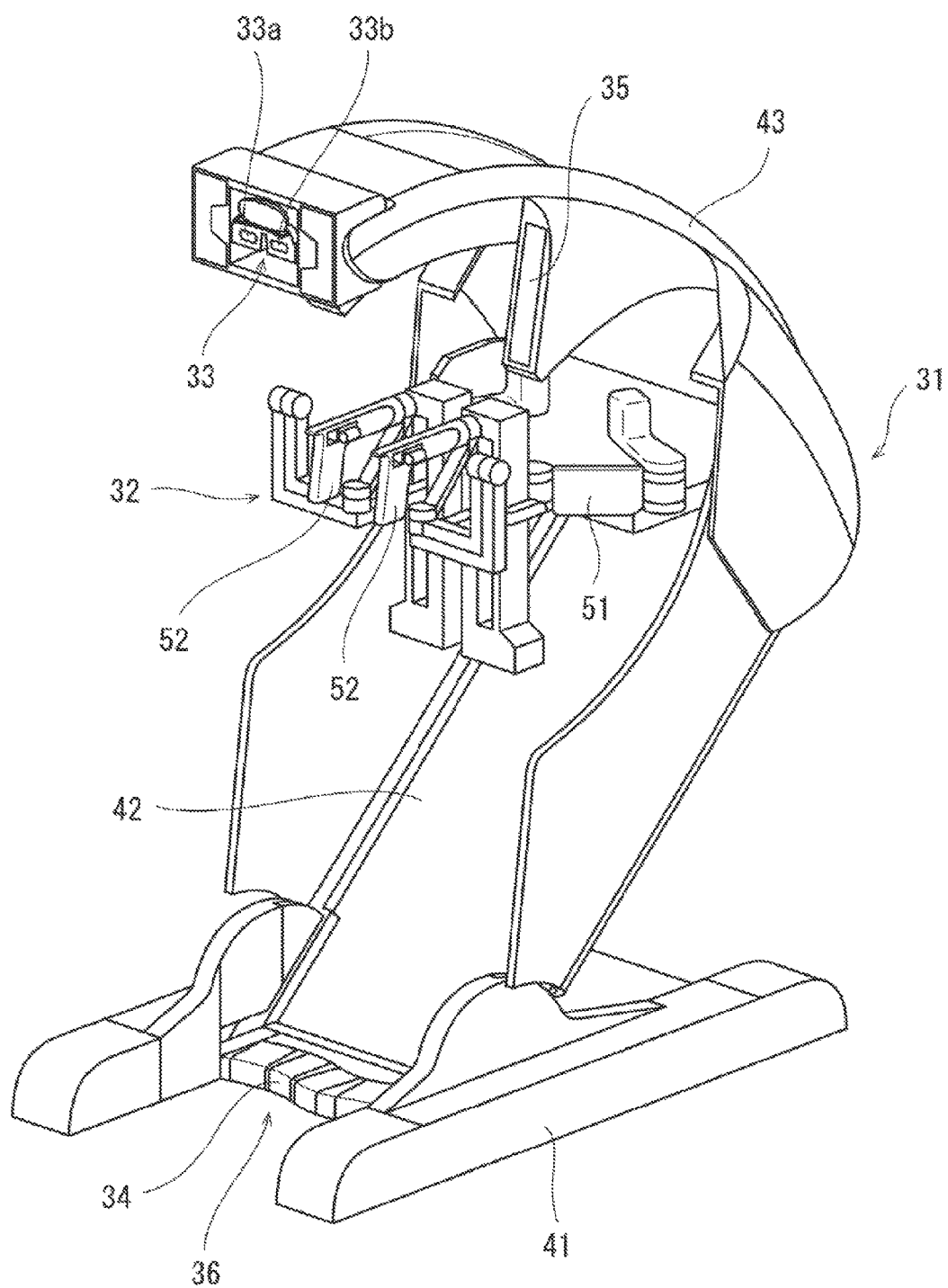
FIG. 2 is a diagram illustrating a perspective view of an example configuration of a remote control apparatus of a remote surgical system, such as the remote surgical system illustrated in FIG. 1.

FIG. 2 is diagram illustrating a perspective view of an example configuration of the remote control apparatus 2.

As illustrated in FIG. 2, the remote control apparatus 2 may include a support mechanism 31, a remote control section 32, a display section 33, and a controller 6 (see e.g., FIG. 4). The remote control apparatus 2 may further include an operation pedal 36 including an operation target switching section 34, and a position control section 35.

The support mechanism 31 may include a support base 41, a lower support 42, an upper support 43, and a joint actuator 44 (see e.g., FIG. 4).

Figure 3A:
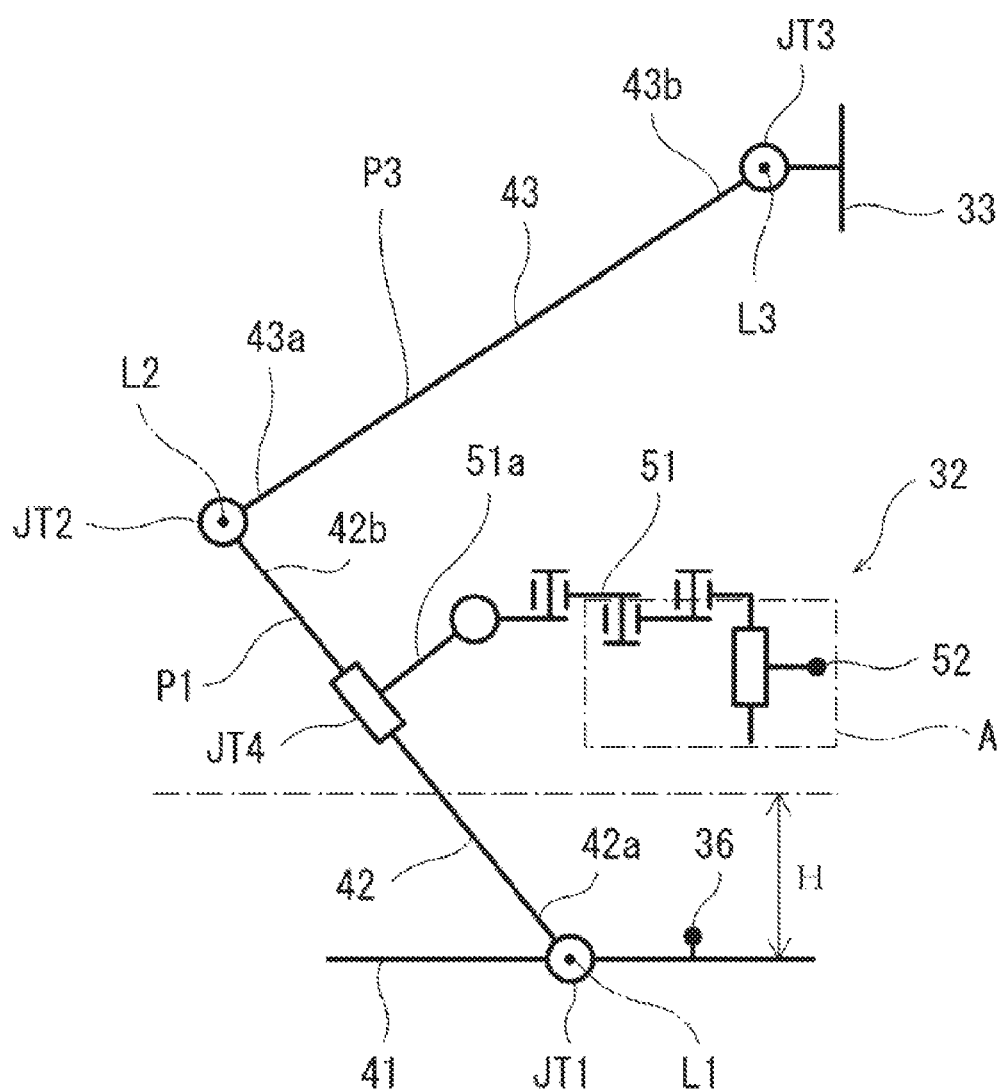
FIG. 3A is a diagram schematically illustrating a side view of an example configuration of a remote control apparatus in a seated position posture in a remote surgical system in accordance with one or more embodiments.
Figure 3B:
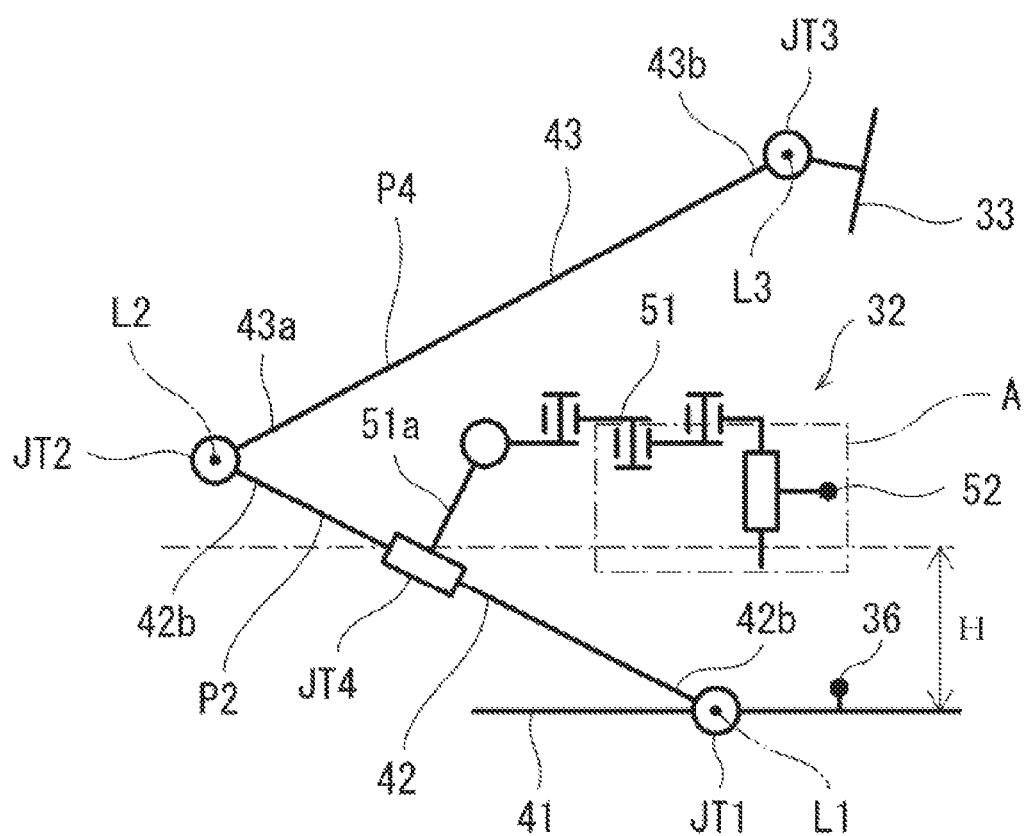
FIG. 3B is a diagram schematically illustrating a side view of an example configuration of a remote control apparatus in a standing position posture in a remote surgical system in accordance with one or more embodiments.

FIG. 3A is a diagram schematically illustrating a side view of an example configuration of the remote control apparatus 2 in a standing position posture, which will be described later. FIG. 3B is a diagram schematically illustrating a side view of an example configuration of the remote control apparatus 2 in a seated position posture, which will be described later.

As illustrated in FIGS. 2, 3A and 3B, the support base 41 may comprise a pair of left and right legs extending in the fore-aft directions. The support base 41 of the remote control apparatus 2 installed in an operating room contacts on the floor surface of the operating room.

As illustrated in FIGS. 3A and 3B, the lower support 42 has a proximal end 42a attached approximately at the longitudinal middle of the support base 41. The proximal end 42a of the lower support 42 is attached to the support base 41 so that it is able to pivot about an axis (e.g., a first axis L1) extending in the horizontal direction (i.e., the leftward and rightward directions as viewed from the operator O). The proximal end 42a is configured to be able to place the lower support 42 at least at any angle position between a standing angle position P1, where the lower support 42 extends obliquely upward and forward from the support base 41 as shown in FIG. 3A, and a leaning angle position P2 as shown in FIG. 3B. To get to the leaning angle position P2, the lower support 42 is rotated forward from the standing angle position P1. The connecting portion between the support base 41 and the proximal end 42a of the lower support 42 functions as a first joint JT1. The standing angle position P1 and the leaning angle position P2 are determined by the angle of the first joint JT1.

The upper support 43 has a proximal end 43a attached to a distal end 42b of the lower support 42. The proximal end 43a of the upper support 43 is attached to the distal end 42b of the lower support 42 so that it is able to pivot about an axis (e.g., a second axis L2) extending in the horizontal direction (i.e., the leftward and rightward directions as viewed from the operator O). The proximal end 43a is configured to be able to place the upper support 43 at least at any angle position between a wide angle position P3, where the upper support 43 extends obliquely upward and backward from the distal end 42b of the lower support 42 at the standing angle position P1 shown in FIG. 3A, and a narrow angle position P4 shown in FIG. 3B where a smaller angle is formed between the upper support 43 and the lower support 42 than when the upper support 43 is at the wide angle position P3. The connecting portion between the distal end 42b of the lower support 42 and the proximal end 43a of the upper support 43 functions as a second joint JT2. The wide angle position P3 and the narrow angle position P4 are determined by the angle of the second joint JT2.

The display section 33 is provided at the distal end 43b of the upper support 43 so as to face the operator O. The display section 33 is configured to be rotatable about an axis (e.g., a third axis L3) extending in the horizontal direction (i.e., the leftward and rightward directions as viewed from the operator O). The connecting portion between the distal end 43b of the upper support 43 and the display section 33 functions as a third joint JT3.

In one or more embodiments, in accordance with one or more embodiments, the first to third axes L1, L2 and L3 may be approximately parallel to one another.

FIG. 4 is a block diagram illustrating an example configuration of a control system of the remote surgical system 100.

As illustrated in FIG. 4, the joint actuator 44 may include a first joint actuator 45, a second joint actuator 46, and a third joint actuator 47. The first joint actuator 45 actuates the first joint JT1 to change the angle position of the lower support 42 relative to the support base 41. The second joint actuator 46 actuates the second joint JT2 to change the angle position of the upper support 43 relative to the lower support 42. The third joint actuator 47 actuates the third joint JT3 to change the angle position of the display section 33 relative to the upper support 43.

As illustrated in FIGS. 2, 3A, 3B and 4, the remote control section 32 is operated to input movement type instructions to be executed by the instrument arms 3 and the camera arm 4. The remote control section 32 may include an operation arm 51.

The remote surgical system 100 serves as a master-slave system in controlling the movements of the instrument arms 3 and the camera arm 4. Specifically, the operation arm 51 serves as a master controlling element in the master-slave system, and the instrument arms 3 and the camera arm 4 serve as slave moving elements. When the operator O operates a handle (e.g., an operating handle or the like) 52 of the operation arm 51, the remote surgical system 100 controls the movement of the instrument arms 3 or the camera arm 4 so that the distal end of each instrument arm 3 (i.e., the end effector of the instrument 12) or the distal end of the camera arm 4 (i.e., the endoscope camera probe 13) will trace the movement of the handle 52 and shift accordingly. Note that the remote surgical system 100 is not limited to the master-slave system.

The remote surgical system 100 in accordance with one or more embodiments may be configured to control the movements of the respective instrument arms 3 according to a movement scale factor which has been set. For example, in a case in which the movement scale factor has been set to be ½, the end effector of the instrument 12 is controlled to shift by one half (½) of a distance by which the handle 52 has shifted, which enables a fine level of accuracy for a surgery.

The operation arm 51 is attached to the lower support 42 such that it is located behind (i.e., inside) the lower support 42. Specifically, the operation arm 51 extends toward the operator O, with a proximal end 51a thereof attached to the lower support 42 and the handle 52 provided at a distal end of the operation arm 51. A plurality of joints may be provided between the proximal end 51a and the handle 52. The handle 52 is configured to be movable within a predetermined three-dimensional operation area A (see e.g., FIGS. 3A and 3B) with respect to the proximal end 51a of the operation arm 51. In other words, the handle 52 is movable in the upward and downward directions, leftward and rightward directions, and forward and backward directions with respect to the proximal end 51a. Each of the joints between the proximal end 51a and the handle 52 is provided with a detector (not shown), which detects a positional relationship between the respective joints. The detector may be, for example, an encoder or a resolver, which may be used to detect a position of the handle 52 relative to the proximal end 51a.

The handle 52 is also configured to be able to move, for example, upward and downward about 15 cm each (about 30 cm in total) from a center position C with respect to the proximal end 51a. In such a case, if the movement scale factor is set to be ½, the instrument arm 3 can move approximately 15 cm in total in the upward and downward directions, resulting in maintaining smooth operation of the remote surgical system 100.

As mentioned earlier, the operation arm 51 extends toward the operator O, with its proximal end 51a attached to the lower support 42. Thus, moving the lower support 42 from the standing angle position P1 to the leaning angle position P2 allows the operation arm 51 to shift obliquely forward and downward relative to the support base 41 or the operation pedal 36. Similarly, moving the operation arm 51 from the leaning angle position P2 to the standing angle position P1 allows the operation arm 51 to shift obliquely backward and upward relative to the support base 41 or the operation pedal 36.

In one or more embodiments, the proximal end 51a of the operation arm 51 is attached to the lower support 42 so as to be slidable in the extending direction of the lower support 42 on a side view. The connecting portion between the proximal end 51a of the operation arm 51 and the lower support 42 functions as a fourth joint JT4. The height of the operation arm 51 can thereby be finely adjusted by sliding the operation arm 51 with respect to the lower support 42 when the angle position of the lower support 42 with respect to the support base 41 is changed.

The display section 33 can display images taken by the endoscope camera probe 13.

In one or more embodiments, the display section 33 may be, for example, a three-dimensional display which is configured to allow the operator O to view the images, which are being taken by the endoscope camera probe 13, stereoscopically by presenting a different image to each eye of the operator O. The display section 33 may include a left-eye display section 33a and a right-eye display section 33b defined as separate sections, where different images are presented to the eyes of the operator O, who may bring their face close to the display section 33 to view the image displayed on the left-eye display section 33a with a left eye, and simultaneously view the image displayed on the right-eye display section 33b with a right eye.

In some embodiments, the operator O may be allowed to view the images that are being taken by the endoscope camera probe 13 stereoscopically, using a known 3D viewing technique, such as one using a polarizing glass or one using an active shutter glass.

As previously described, the display section 33 may be provided at the distal end 43b of the upper support 43 so as to face the operator O. Such a configuration allows the display section 33 to be shifted downward by moving the upper support 43 from the wide angle position P3 to the narrow angle position P4, and also to be shifted upward by moving the upper support 43 from the narrow angle position P4 to the wide angle position P3.

The operation target switching section 34 is a controlling element that may allow the operator O to input an operation target switching instruction that the target to be controlled by the operation arm 51 be switched between any one of the instrument arms 3 and the camera arm 4. The operation target switching section 34 may be an operation pedal attached to the support base 41. If the camera view needs to be changed during the surgery, the operator O operates the operation target switching section 34 to switch the target to be controlled by the operation arm 51 from the instrument arm 3 to the camera arm 4, and controls the operation arm 51 to shift the endoscope camera probe 13. After having shifted the endoscope camera probe 13, the operator O operates the operation target switching section 34 again to switch the target to be controlled by the operation arm 51 from the camera arm 4 back to the instrument arms 3, and continues the surgery.

Figure 5:
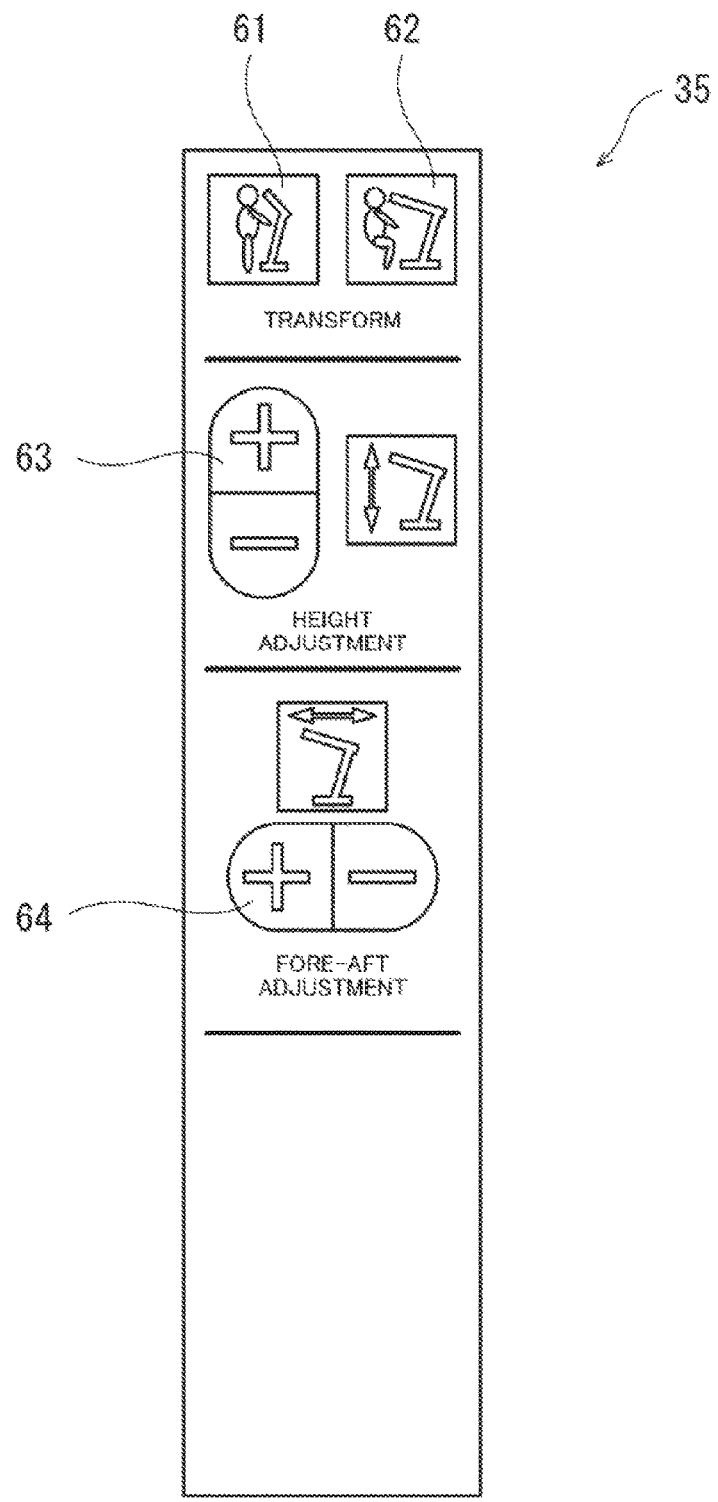
FIG. 5 is a diagram illustrating an example configuration of a position control section for a remote control apparatus of a remote surgical system in accordance with one or more embodiments.

FIG. 5 illustrates an example configuration of the position control section 35.

The position control section 35 is a controlling element allowing the operator O to input a position change instruction that the position of the support mechanism 31 be switched between a one suitable for a standing position and a one suitable for a seated position. As illustrated in FIGS. 2 and 5, the position control section 35 has a plurality of operation buttons, and is attached to the upper support 43.

As illustrated in FIG. 5, the position control section 35 may include a button 61 to transform the support mechanism 31 to the standing position posture, and a button 62 to transform the support mechanism 31 to the seated position posture. The position control section 35 also may include a height adjustment button 63 and a fore-aft adjustment button 64.

The button 61 is used to input an instruction to transform the support mechanism 31 to the standing position posture (e.g., a first posture). The button 62 is used to input an instruction to transform the support mechanism 31 to the seated position posture (e.g., a second posture). The standing position posture and the seated position posture will be described in detail later.

The height adjustment button 63 is used to input an instruction to change the angle position of the upper support 43 with respect to the lower support 42. As mentioned earlier, the vertical position of the display section 33 can be changed by changing the angle position of the upper support 43 with respect to the lower support 42. The fore-aft adjustment button 64 is used to input an instruction to change the angle position of the upper support 43 with respect to the support base 41. As mentioned earlier, the positions of the display section 33 and the operation arm 51 in the fore-aft direction can be changed by changing the angle position of the lower support 42 with respect to the support base 41.

Example Configuration of Controller

As illustrated in FIG. 4, the controller 6 may include, for example, a control section 66 having an arithmetic unit, e.g., a central processing unit (CPU), a processor, a controller or the like), and a storage section 67 having a memory, e.g., a ROM and a RAM. The controller 6 may be configured as a single controller which provides centralized control, or may be configured as a plurality of controllers which work in cooperation with each other and provide distributed control.

The control section 66 determines whether the movement type instruction received by the remote control section 32 is an instruction to be executed by the instrument arms 3, or an instruction to be executed by the camera arm 4, according to the switched state of the operation target switching section 34. If the control section 66 determines that the movement type instruction received by the remote control section 32 is an instruction to be executed by the instrument arms 3, the control section 66 transmits this movement type instruction to the instrument arms 3. In response, the remote control apparatus 2 controls the instrument arms 3 of the patient-side surgery apparatus 1 to shift and position the respective instruments 12.

Alternatively, if the control section 66 determines that the movement type instruction received by the remote control section 32 is an instruction to be executed by the camera arm 4, the control section 66 transmits this movement type instruction to the camera arm 4. In response, the remote control apparatus 2 controls the camera arm 4 of the patient-side surgery apparatus 1 to shift and position the endoscope camera probe 13.

Furthermore, the control section 66 controls the joint actuator 44 according to the position change instruction received by the position control section 35, thereby controlling the angles of the first joint JT1, the second joint JT2, and the third joint JT3.

The control section 66 receives the images taken by the endoscope camera probe 13 from the endoscope camera probe 13, and processes the images so that they can be displayed on the display section 33.

The storage section 67 stores predetermined control programs, which are read out and executed by the control section 66 to control the movement of the remote surgical system 100. The storage section 67 also stores information on the angles of the first joint JT1, the second joint JT2, and the third joint JT3 in the standing position posture, and those in the seated position posture.

The information relating to the angles of the standing position posture and the seated position posture may be stored as default values of the remote control apparatus 2. The default values may be adjusted by the operator O every time they use the remote control apparatus 2, or the information may be changed so that the information relating to the angles of the standing position posture and the seated position posture can be defined as different values. Alternatively, the information relating to the angles of the standing position posture and the seated position posture may be stored for each individual operator O so that multiple different operators O can use the same remote control apparatus 2.

Example Configuration of Standing Position Posture

FIG. 6A is diagram illustrating a side view of an example configuration of the remote control apparatus 2 in the standing position posture.

As illustrated in FIG. 6A, the standing position posture according to one or more embodiments is a posture in which the lower support 42 takes the standing angle position P1, and the upper support 43 takes the wide angle position P3.

The standing angle position P1 of the lower support 42 may be determined such that the operation arm 51 is located at a vertical position suitable for the operator O in the standing position to grip the handle 52 at the center position C with the arms of the operator bent at approximately right angles.

The wide angle position P3 of the upper support 43 is determined such that the display section 33 is located at a vertical position suitable for the operator O in the standing position to view the image on the display section 33.

The standing position posture may also be a posture in which the display section 33 is oriented in a direction suitable for the operator O in the standing position to view the image on the display section 33. In this case, the angle position of the display section 33 with respect to the upper support 43, that is, the angle of the third joint JT3, is determined so that the display section 33 is oriented in a direction suitable for the operator O in the standing position to view the image on the display section 33.

In an operating room, a zone covering a range with a height H of up to 70 cm from the floor surface is specified as the contaminated zone. Thus, in one or more embodiments, the remote control apparatus 2 may be configured based on an ergonomics human model such that the entire operation area A of the handle 52 in the standing position posture may be included in a clean zone, which may be located at and above a height of 70 cm from the floor surface. Thus, during a surgery a treatment using the instrument arms 3 and a manually performed treatment may be alternately conducted by the operator O, using the remote control apparatus 2 in the standing position posture, which may prevent the contamination of the operating handle and the hands of the operator O. The operator O may thereby be allowed to switch from the operating handle to a surgical instrument quickly, and to continue the surgery while standing, without going through additional cleaning procedure.

Example Configuration of Seated Position Posture

FIG. 6B is a diagram illustrating a side view of an example configuration of the remote control apparatus in the seated position posture.

As illustrated in FIG. 6B, the seated position posture is a posture at which the lower support 42 takes the leaning angle position P2 and the upper support 43 takes the narrow angle position P4. The leaning angle position P2 of the lower support 42 is determined such that the operation arm 51 is located at a vertical position suitable for the operator O sitting on a chair to grip the handle 52 at the center position C with arms bent at approximately right angles.

The narrow angle position P4 of the upper support 43 is determined such that the display section 33 is located at a vertical position suitable for the operator O sitting on a chair to view the image on the display section 33.

The seated position posture may also be a posture in which the display section 33 is oriented in a direction suitable for the operator O sitting on a chair to view the image on the display section 33. In this case, the angle position of the display section 33 with respect to the upper support 43, that is, the angle of the third joint JT3, is determined so that the display section 33 is oriented in a direction suitable for the operator O sitting on a chair to view the image on the display section 33.

In the case of a long surgery using the remote surgical system 100, performing a surgery in a seated position will reduce the accumulation of fatigue of the operator O who performs the surgery.

In the operating room, a zone covering a range with a height H of up to 70 cm from the floor surface, is specified as the contaminated zone. The remote control apparatus 2 may be configured based on an ergonomics human model, such that at least part of the operation area A of the handle 52 is included in the contaminated zone in the seated position posture. Thus, the operator O needs to sterilize their hands in the cleaning procedure if the operator O provides manual treatment directly on a patient P after operating the handle 52 of the remote control apparatus 2 in the seated position posture.

As can be seen, the operator O can change position from standing to seated position or from seated to standing position when operating the remote control apparatus 2, allowing the operator O to operate the remote control apparatus 2 while in a position the operator likes.

In the standing position posture, the position of the handle 52 in the fore-aft direction may be determined such that the operation arm 51 is located at a suitable position for the operator O standing near the pedal of the operation target switching section 34 to grip the handle 52 at the center position C with his/her arms bent at approximately right angles. Also, in the standing position posture, the position of the display section 33 in the fore-aft direction may be determined such that it is located at a suitable position for the operator O standing near the pedal of the operation target switching section 34 to view the image on the display section 33.

On the other hand, in the seated position posture, the position of the handle 52 in the fore-aft direction may be determined such that the operation arm 51 is located at a suitable position for the operator O, sitting on a chair with his/her feet near the pedal of the operation target switching section 34, to grip the handle 52 with his/her arms bent at approximately right angles. Also, in the seated position posture, the position of the display section 33 in the fore-aft direction may be determined such that it is located at a suitable position for the operator O, sitting on a chair with his/her feet near the pedal of the operation target switching section 34, to view the image on the display section 33.

The settings of the standing position posture and the seated position posture allow the operator O to operate the remote control apparatus 2 without moving around, i.e., while standing up and sitting down in the same spot. Further, the settings of the standing and seated position postures allow the operator O to change position quickly.

Figure 7:
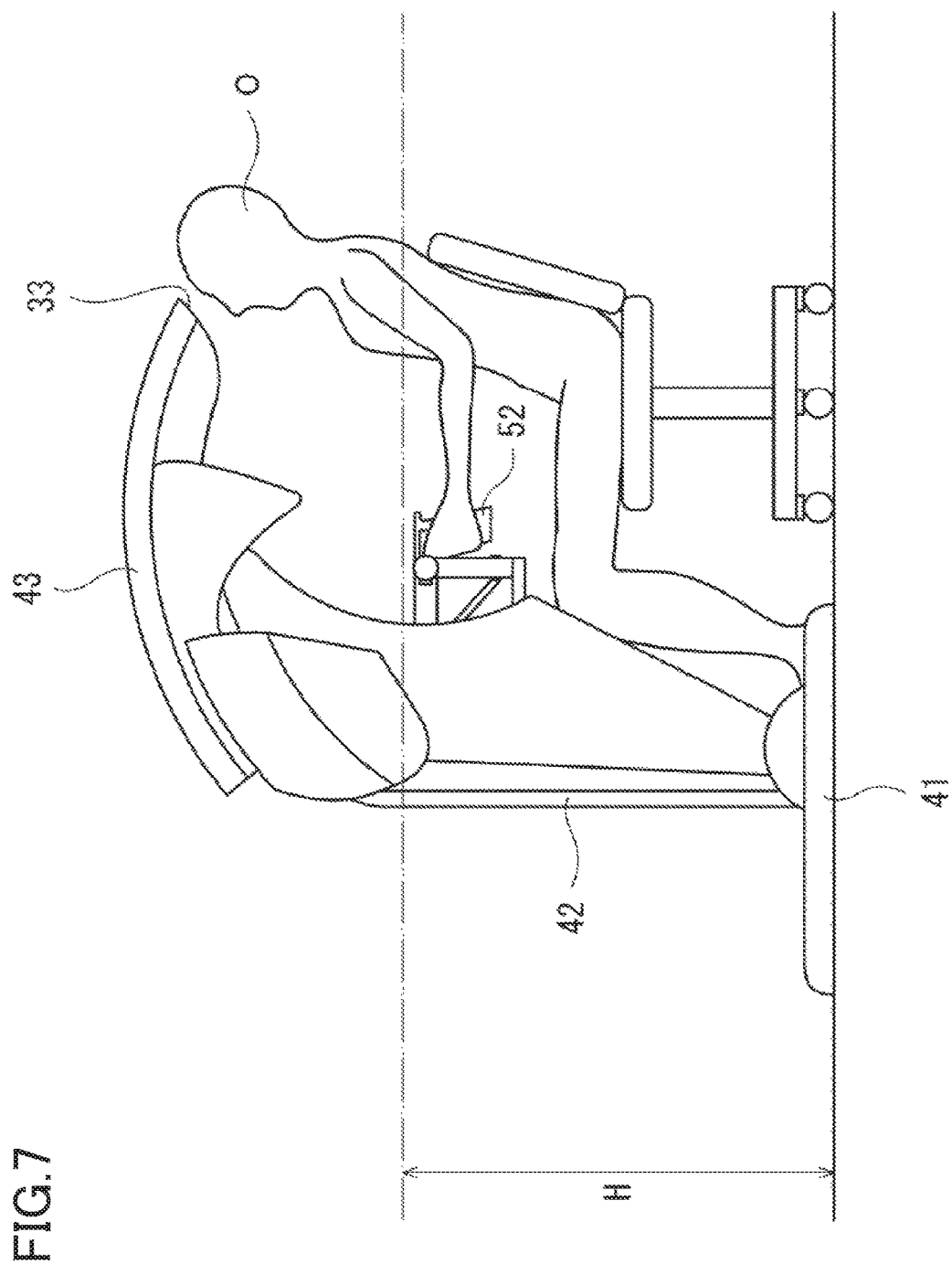
FIG. 7 is a diagram illustrating a side view of an example configuration of a remote control apparatus in another seated position posture in a remote surgical system in accordance with one or more embodiments.

FIG. 7 is a diagram illustrating a side view of an example configuration of the remote control apparatus in another seated position posture.

The operator O may also operate the remote control apparatus 2 in another seated position posture as illustrated in FIG. 7 by controlling the position control section 35 according to operator preference.

Specific Design of Remote Control Apparatus

In one or more embodiments, ergonomic measurement data described in "1988 ANTHROPOMETRIC SURVEY OF U.S. ARMY PERSONNEL: METHODS AND SUMMARY STATISTICS (1988)", which is incorporated by reference herein was used for determining dimensions of the remote control apparatus 2.

In one or more embodiments, Japanese Industrial Standards (JIS) may be used as a reference for ergonomic data for determining dimensions of the remote control apparatus 2. For example, "JIS Z8503-4: 2006 (ISO 11064-4: 2004) Ergonomic design of control centres—Part 4: Layout and dimensions of workstations", which is incorporated by reference herein specifies using the 5th percentile and the 95th percentile of human models, The operation area A is defined as extending upward and downward, 15 cm each, from the center position C. In other words, the dimension of the operation area A in the height direction is defined to be 30 cm. The dimension of the operation area A in the height direction is defined based on the height dimension of the movement area of a surgical instrument which is defined to maintain satisfactory manipulation of the surgical instrument during a laparoscopic surgery, as well as based on the movement scale factor of the handle 52. The defined movement area for the surgical instrument has a height dimension of 15 cm, and the movement scale factor of the handle 52 is ½. Accordingly, the height dimension of the operation area A derived from the height dimension of the movement area of the surgical instrument and the movement scale factor of the handle 52 is 30 cm.

Figure 8A:
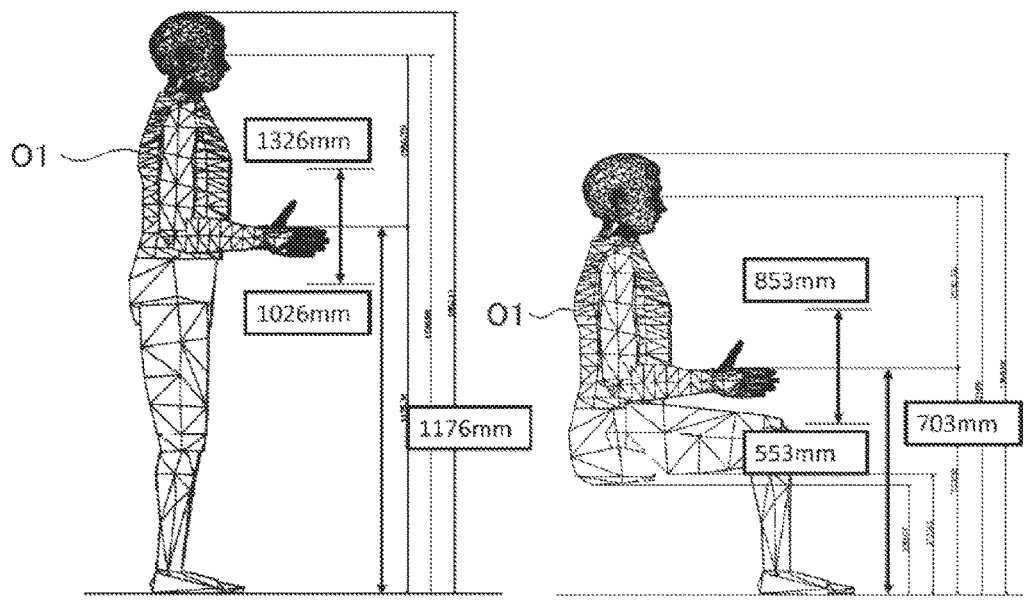
FIG. 8A is a diagram illustrating a large model operator operating a remote surgical system in accordance with one or more embodiments.
Figure 8B:
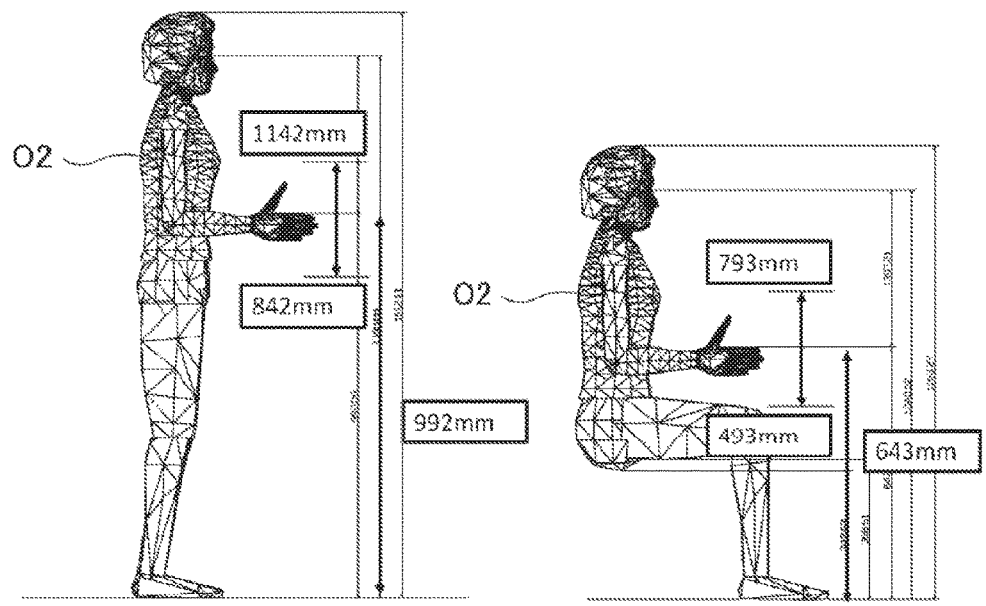
FIG. 8B is a diagram illustrating a small model operator operating a remote surgical system in accordance with one or more embodiments.

FIG. 8A illustrates a model operator O, specifically a large model operator O1. FIG. 8B illustrates another model operator O, specifically a small model operator O2.

In FIG. 8A, body size data of German men were used as the body size data of the large model operator O1. From a group of 100 randomly selected German male models, the fifth largest man model was selected as the model operator O1. In a condition in which model operator O1 holds the handle 52 at the center position C of the operation area A with his arms bent at right angles while in the stand-up position (i.e., the standing position), the vertical position of the handle 52 is about 118 cm, and the lower and upper limits of the vertical position of the operation area A are about 103 cm and about 133 cm, respectively. On the other hand, in a condition in which the model operator O1 holds the handle 52 at the center position C of the operation area A with his arms bent at right angles while sitting on a chair, the vertical position of the handle 52 is about 70 cm from a floor surface, and the lower and upper limits of the vertical position of the operation area A are about 55 cm and about 85 cm, respectively from a floor surface.

Turning to FIG. 8B, body size data of Japanese women were used as the body size data of the small model operator O2. From a group of 100 randomly selected Japanese women models, the fifth smallest woman model was selected as the model operator O2. In a condition in which the model operator O2 holds the handle 52 at the center position C of the operation area A with her arms bent at right angles while in the stand-up position, the vertical position of the handle 52 is about 99 cm, and the lower and upper limits of the vertical position of the operation area A are about 84 cm and about 114 cm, respectively. On the other hand, in a condition in which the model operator O2 holds the handle 52 at the center position C of the operation area A with her arms bent at right angles while sitting on a chair, the vertical position of the handle 52 is about 64 cm, and the lower and upper limits of the vertical position of the operation area A are about 49 cm and about 79 cm, respectively.

Based on these data, the vertical positions of the handle 52 at which a plurality of operators O in different body sizes can smoothly take the standing position or the seated position are as follows.

First, in one or more embodiments, the vertical position of the handle 52 at the center position C of the operation area A in the standing position posture be set to be about 99 cm or more to correspond to the small model operator O2 in the standing position. This configuration allows almost all operators O in the standing position to use the handle 52 comfortably. In this case, in which the handle 52 is configured to be able to move downward by 15 cm from the center position C, the lower limit of the vertical position of the operation area A of the handle 52 in the standing position posture is 84 cm or more, as described above.

Further, in one or more embodiments, the vertical position of the handle 52 at the center position C in the standing position posture be set to be 85 cm or more from the floor surface. In the above-disclosed configuration, in which the handle 52 is configured to be able to move downward by 15 cm from the center position C, the lower limit of the vertical position of the operation area A of the handle 52 in the standing position posture is 70 cm or more from the floor surface, meaning that the operation area A of the handle 52 is included in the clean zone. The operator O can therefore switch from the operating handle to a surgical instrument quickly when needed, and continue the surgery without going through a cleaning procedure. In other words, when operating the remote control apparatus 2 while taking the standing position, the operator O can temporarily stop operating the remote control apparatus 2 and immediately provide the surgery directly on the patient. The operator O can also move to the patient and give the patient a treatment manually while operating the remote control apparatus 2 simultaneously. Here, the lower limit of the vertical position of the operation area A which corresponds to the small model operator O2 in the standing position is about 84 cm, as mentioned above. Hence, much more operators O in different body sizes can operate the handle 52 comfortably in the standing position by setting the lower limit of the vertical position of the operation area A to be 70 cm above the floor surface.

Next, in one or more embodiments, the vertical position of the handle 52 at the center position C of the operation area A in the seated position posture be set to be about 64 cm or more to correspond to the small model operator O2 in the seated position. Such a configuration allows almost all operators O in the seated position to use the handle 52 comfortably.

Next, in one or more embodiments, the displacement (i.e., an adjustment range) of the vertical position of the handle 52 when the remote control apparatus 2 transforms between the standing position posture and the seated position posture, be equal to or more than about 35 cm, which is the difference between about 99 cm that is the vertical position of the handle 52 at the center position C corresponding to the small model operator O2 in the standing position, and about 64 cm that is the vertical position of the handle 52 at the center position C corresponding to the small model operator O2 in the seated position.

Further, in one or more embodiments, the displacement of the vertical position of the handle 52 when the remote control apparatus 2 transforms between the standing position posture and the seated position posture, be equal to or more than about 48 cm, which is the difference between about 118 cm that is the vertical position of the handle 52 at the center position C corresponding to the large model operator O1 in the standing position (in other words, the highest position of the handle 52 at the center position C in the standing position posture when the handle 52 is used by this large model operator O1) and about 70 cm that is the vertical position of the handle 52 at the center position C corresponding to the large model operator O1 in the seated position.

As can be seen from the above described examples, the adjustment range of the vertical position of the handle 52 when the remote control apparatus 2 transforms between the standing position posture and the seated position posture is larger than the adjustment range that is desirably ensured so that the remote control apparatus 2 in the standing position posture can adjust to the body size of the operator. For example, the adjustment range may be larger than about 19 cm representing the difference between the vertical position of the handle 52 at the center position C corresponding to the large model operator O1 and the vertical position of the handle 52 at the center position C corresponding to the small model operator O2. The adjustment range of the vertical position of the handle 52 when the remote control apparatus 2 transforms between the standing position posture and the seated position posture may also be larger than the adjustment range that the remote control apparatus 2 in the seated position posture that can be used to adjust to the body size of the operator. For example, the adjustment range may be larger than about 6 cm representing the difference between the vertical position of the handle 52 at the center position C corresponding to the large model operator O1 and the vertical position of the handle 52 at the center position C corresponding to the small model operator O2.

The above described adjustment range may be further increased in a condition in which the position of the handle 52 is set to be higher than about 118 cm representing the vertical position of the handle 52 at the center position C corresponding to the large model operator O1 in the standing position.

In one or more embodiments, the adjustment range may be equal to or more than 50 cm from the vertical position of the handle 52 in the standing position posture.

Further, in one or more embodiments, the displacement of the vertical position of the handle 52 when the remote control apparatus 2 transforms between the standing position posture and the seated position posture may be equal to or more than about 54 cm, which is the difference between about 118 cm that is the vertical position of the handle 52 at the center position C corresponding to the large model operator O1 in the standing position and about 64 cm, which is the vertical position of the handle 52 at the center position C corresponding to the small model operator O2 in the seated position.

In one or more embodiments as disclosed herein above, the operation area A may be defined as having a vertical width of 30 cm. However, the dimensions of the operation area A may be changed to have a vertical width of, e.g., 20 cm, 25 cm, or 35 cm, with the size of the handle 52, for example, taken into consideration.

Example Movements

Now, example movements of the remote control apparatus 2 will be described.

To transform the remote control apparatus 2 from the standing position posture to the seated position posture, the operator O presses the button 62 to input an instruction to transform the support mechanism 31 to the seated position posture.

In a condition in which the control section 66 receives the instruction to transform the support mechanism 31 to the seated position posture, the control section 66 reads information on the angles of the first joint JT1, the second joint JT2, and the third joint JT3 for the seated position posture from the storage section 67.

The control section 66 may control the first joint actuator 45 to move the lower support 42 and change the angle position of the lower support 42 from the standing angle position P1 to the leaning angle position P2. As a result of the controlled movement, the handle 52 shifts down, allowing the vertical position of the handle 52 to be adjusted so as to correspond to the vertical position of the downward shifted hands of the operator O who has changed position from the stand-up position (i.e., the standing position) to the sitting-on-chair position (i.e., the seated position). The position of the display section 33 may also be shifted down, allowing the vertical position of the display section 33 to be adjusted so as to correspond to the vertical position of the downward shifted eyes of the operator O who has changed position from the stand-up position to the sitting-on-chair position.

The control section 66 may further control the second joint actuator 46 to move the upper support 43 and change the angle position of the upper support 43 from the wide angle position P3 to the narrow angle position P4. As a result, the display section 33 may be further shifted down, allowing the vertical position of the display section 33 to be adjusted so as to correspond to the vertical position of the downward shifted eyes of the operator O who has changed position from the stand-up position to the sitting-on-chair position.

Next, to transform the remote control apparatus 2 from the seated position posture to the standing position posture, the operator O presses the button 61 to input an instruction to transform the support mechanism 31 to the standing position posture.

In a condition in which the control section 66 receives the instruction to transform the support mechanism 31 to the standing position posture, the control section 66 reads information on the angles of the first joint JT1, the second joint JT2, and the third joint JT3 for the standing position posture from the storage section 67.

The control section 66 may control the first joint actuator 45 to move the lower support 42 and change the angle position of the lower support 42 from the leaning angle position P2 to the standing angle position P1. As a result, the handle 52 may be shifted up, allowing the vertical position of the handle 52 to be adjusted so as to correspond to the vertical position of the upward shifted hands of the operator O who has changed position from the sitting-on-chair position to the stand-up position. The display section 33 may also be shifted up, allowing the vertical position of the display section 33 to be adjusted so as to correspond to the vertical position of the upward shifted eyes of the operator O who has changed position from the sitting-on-chair position to the stand-up position.

The control section 66 may further control the second joint actuator 46 to move the upper support 43 and change the angle position of the upper support 43 from the narrow angle position P4 to the wide angle position P3. As a result, the display section 33 may be further shifted up, allowing the vertical position of the display section 33 to be adjusted so as to correspond to the vertical position of the upward shifted eyes of the operator O who has changed position from the sitting-on-chair position to the stand-up position.

Figure 9:
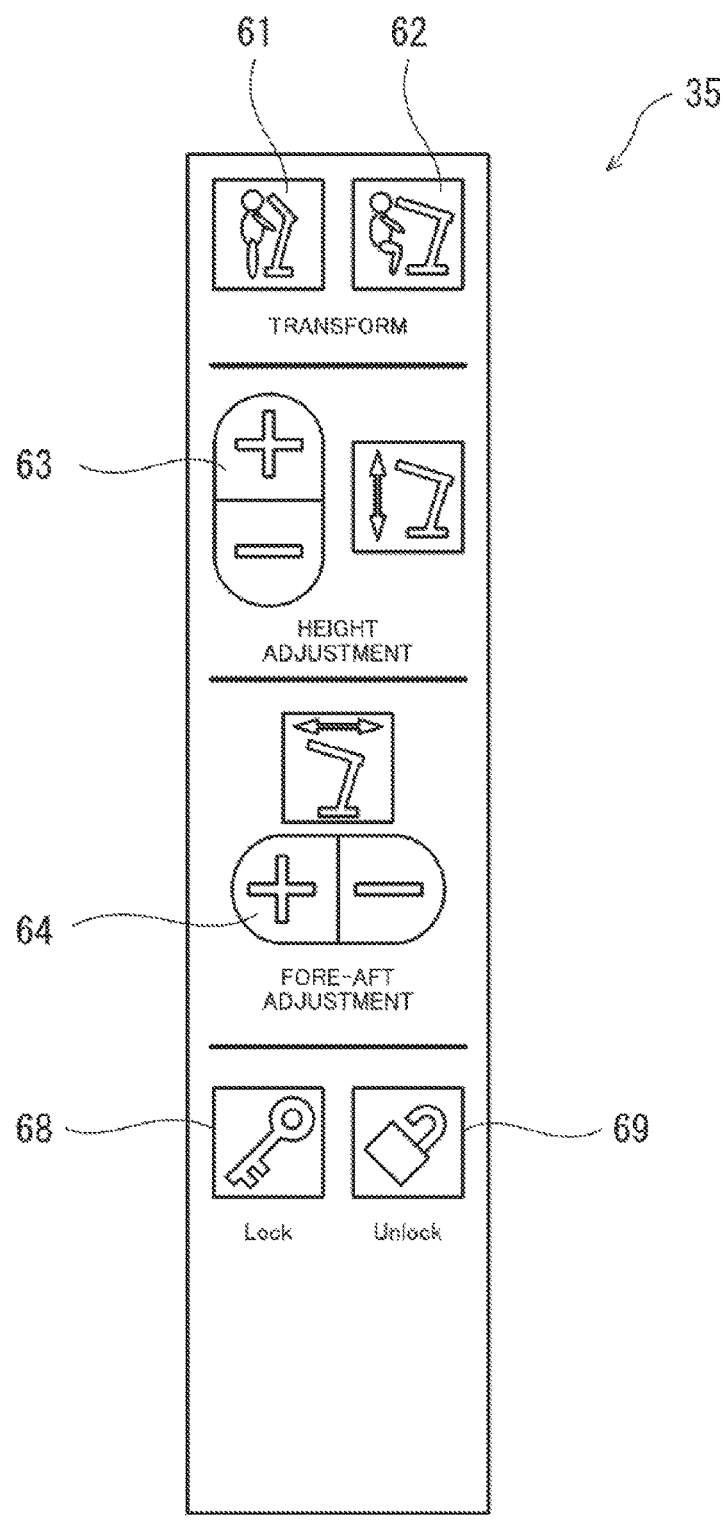
FIG. 9 is a diagram illustrating a variation of a position control section for a remote control apparatus of a remote surgical system in accordance with one or more embodiments.

In one or more embodiments, such as embodiments described above, the positions are switched between the standing position posture and the seated position posture by pressing the transform-to-standing-position-posture button 61 and the transform-to-seated-position-posture button 62. Alternatively, the positions of the lower support 42 and the upper support 43 may be changed manually. In a condition in which the positions are changed manually, each of the lower support 42 and the upper support 43 is provided with a grip such as a lever, and a locking section 71 which locks the angle position of the lower support 42 with respect to the support base 41 and the angle position of the upper support 43 with respect to the lower support 42. Further, the position control section 35 may be provided with a lock button 68 and an unlock button 69 as illustrated in FIG. 9. The lock button 68 is used to input an instruction to lock the position by the locking section 71. The unlock button 69 is used to input an instruction to unlock the position locked by the locking section 71.

Figure 10:
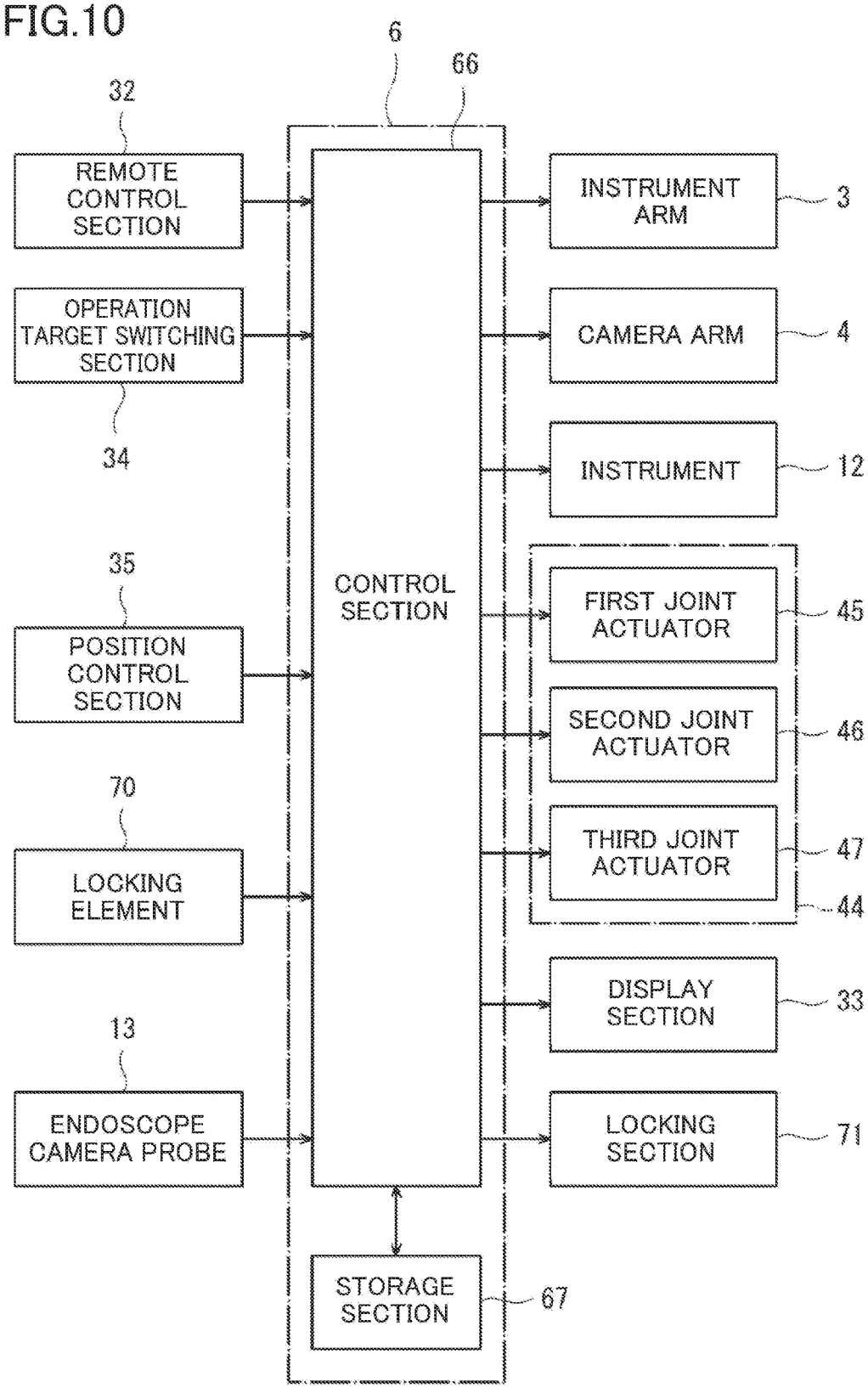
FIG. 10 is a block diagram illustrating a variation of a control system of a remote surgical system in accordance with one or more embodiments.

As illustrated in FIG. 10, an instruction which has been input to a locking element 70 including the lock button 68 and the unlock button 69 may be input to the control section 66, which then controls the locking section.

Thus, the position is locked and unlocked by operating the lock button 68 and the unlock button 69, respectively, before the posture can be transformed manually by holding and moving the grip. The locking section 71 may be implemented as a braking mechanism or a latching mechanism, for example.

As can be seen from the foregoing description, the remote control apparatus 2 may be configured to transform or to be able to transform between the standing position posture and the seated position posture. Thus, the remote control apparatus 2 in the standing position posture allows the operator O to handle the remote control apparatus 2 while in the stand-up position. Similarly, the remote control apparatus 2 in the seated position posture allows the operator O to handle the remote control apparatus 2 while in the sitting-on-chair position. That is, the operator O can switch between the standing position and the seated position while handling the remote control apparatus 2, allowing the operator O to handle the remote control apparatus while in a position that the operator desires, prefers or likes.

Second Embodiment

Figure 11:
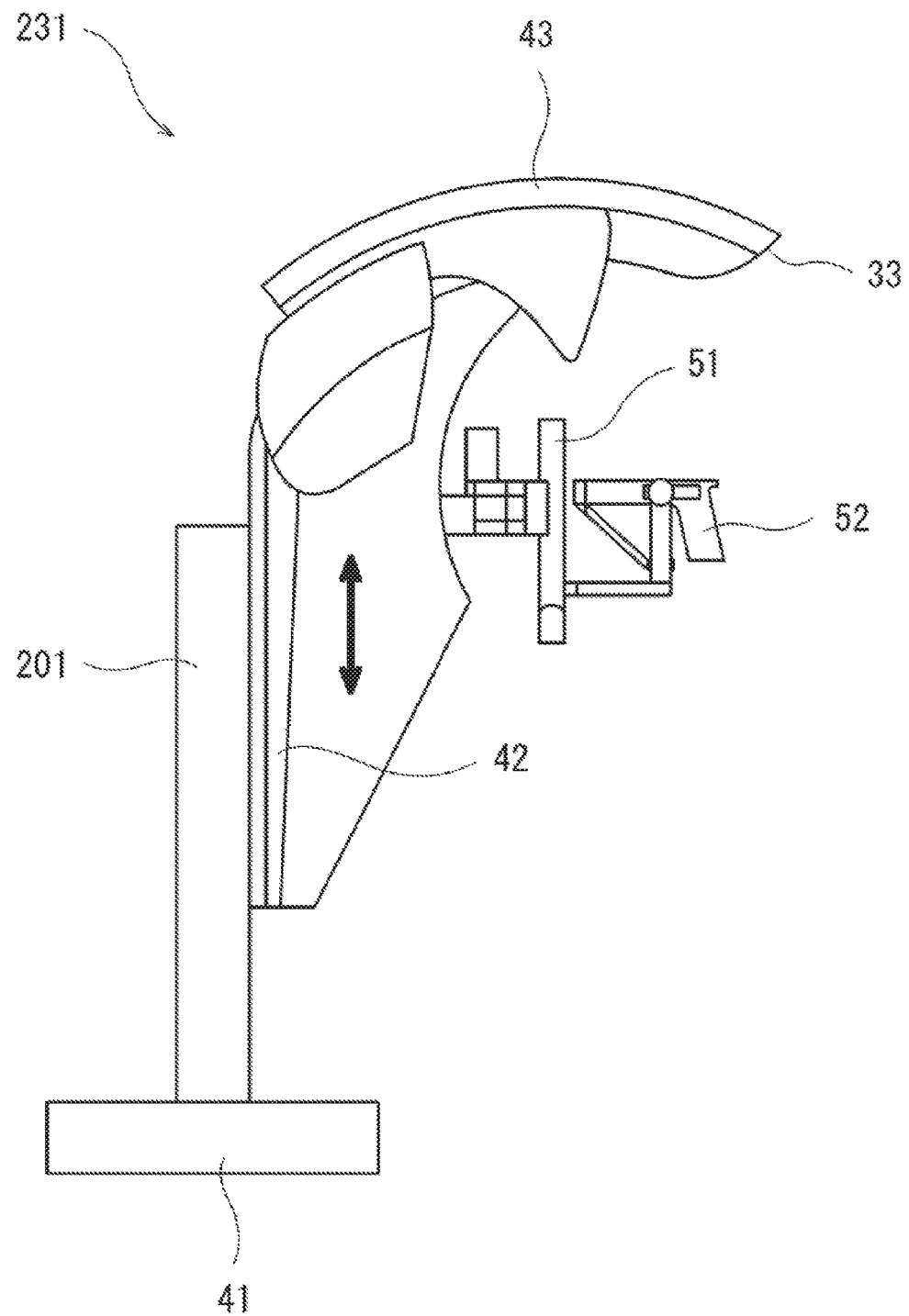
FIG. 11 is a diagram illustrating a side view of an example configuration of a remote control apparatus of a remote surgical system in accordance with one or more embodiments.

FIG. 11 is a diagram illustrating a side view of a remote control apparatus 202 of a remote surgical system 200.

In some embodiments, such as those described above, the support mechanism 31 is transformed from the standing position posture to the seated position posture, and vice versa, by adjusting the angles of the first joint JT1 and the second joint JT2 which are pivotally rotatable joints.

On the other hand, in accordance with one or more embodiments, the support mechanism 231 may be provided in which a first joint JT1 is configured as a slide mechanism (e.g., a prismatic joint) 201 provided between the support base 41 and the lower support 42.

The slide mechanism 201 changes the vertical position of the lower support 42 with respect to the support base 41, and connects the support base 41 and the lower support 42 such that the lower support 42 is slidable up and down (i.e., in the vertical direction) with respect to the support base 41. Further, the first joint actuator 245 moves the slide mechanism 201 to change the vertical position of the lower support 42 with respect to the support base 41.

Figure 12:
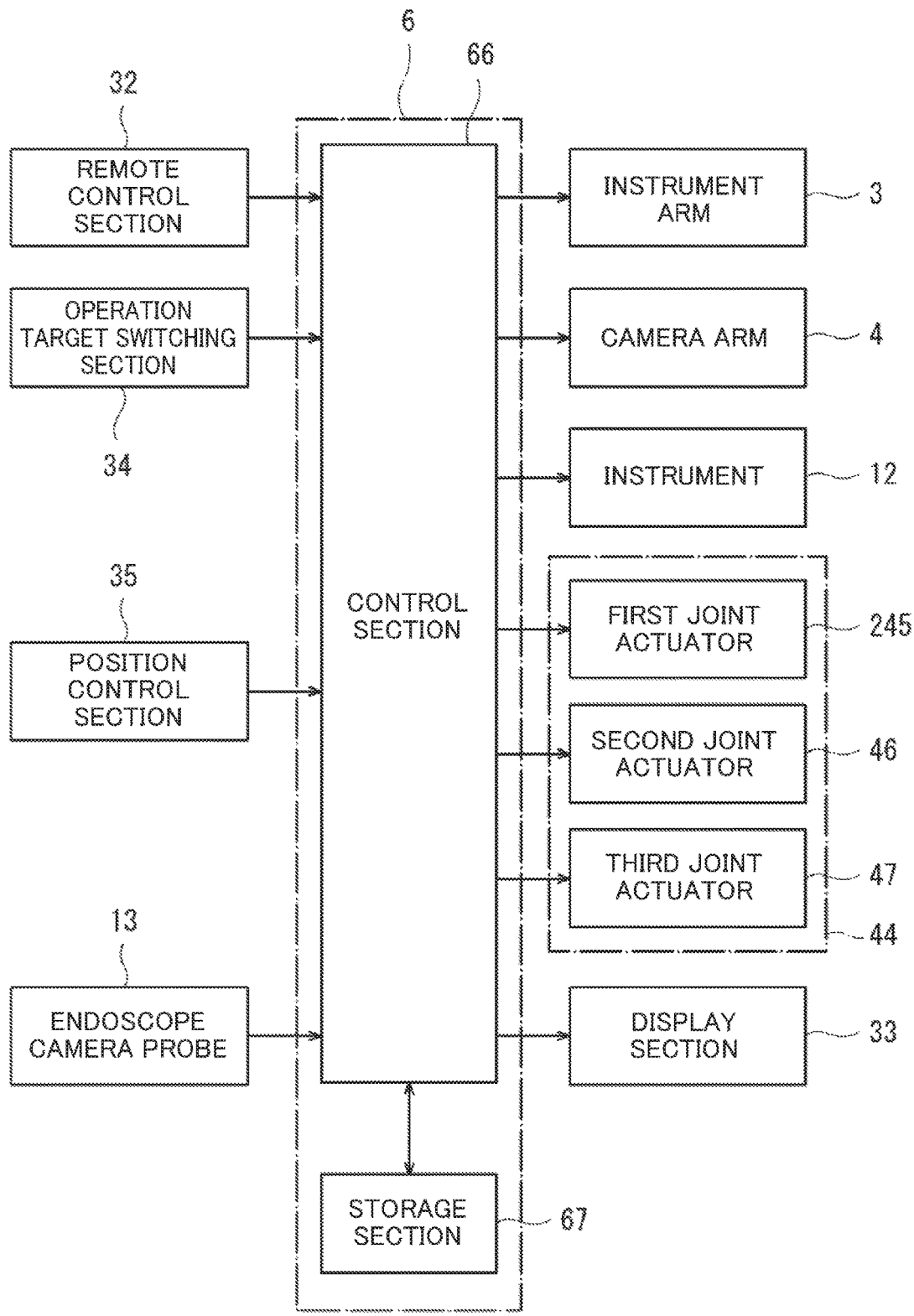
FIG. 12 is a block diagram illustrating an example configuration of a control system of a remote surgical system in accordance with one or more embodiments.

FIG. 12 is a block diagram illustrating an example configuration of a control system of the remote surgical system 200.

Elements of the controller according to one or more embodiments are shown in FIG. 12. The same reference characters are used to designate the elements having the same or similar functions as/to those in the first embodiment.

In one or more embodiments, the control section 66 controls the joint actuator 44 according to a position change instruction input to the position control section 35, and thereby controls the vertical position of the lower support 42 with respect to the support base 41 and the angles of the second joint JT2 and the third joint JT3.

The storage section 67 stores predetermined control programs, which are read out and executed by the control section 66 to control the movement of the remote surgical system 200. The storage section 67 also stores information on the vertical position of the lower support 42 with respect to the support base 41 regarding the first joint JT1, an angle of the second joint JT2, and an angle of the third joint JT3 in the standing position posture, and those in the seated position posture. An example has been described in which the support mechanism 231 comprises the support base 41, the slide mechanism 201, the lower support 42, and the upper support 43. However, the lower support 42 and the upper support 43 may be integrally formed as a support member, and the second joint JT2 may be omitted. Further, the third joint JT3 for adjusting the angle of the display section may also be omitted. In such cases, the standing position posture and the seated position posture may be switched only through the vertical movement of the integrally-formed support member.

Now, an example movement of the remote control apparatus 2 according to one or more embodiments will be described.

To transform the remote control apparatus 2 from the standing position posture to the seated position posture, the operator O presses the button 62 to input an instruction to transform the support mechanism 231 to the seated position posture.

In a condition in which the control section 66 receives the instruction to transform the support mechanism 231 to the seated position posture, the control section 66 reads information on the height of the (lower) support member in the seated position posture and, in some cases, information on the angles of the second joint JT2 and the third joint JT3, from the storage section 67.

The control section 66 may control the first joint actuator 245 to move the (lower) support member and change the height of the (lower) support member from the height for the standing position posture to the height for the seated position posture. As a result, the handle 52 shifts down, allowing the vertical position of the handle 52 to be adjusted so as to correspond to the vertical position of the downward shifted hands of the operator O who has changed position from the stand-up position to the sitting-on-chair position. The display section 33 shifts down, too, allowing the vertical position of the display section 33 to be adjusted so as to correspond to the vertical position of the downward shifted eyes of the operator O who has changed position from the stand-up position to the sitting-on-chair position.

To transform the remote control apparatus 2 from the seated position posture to the standing position posture, the operator O presses the button 61 to input an instruction to transform the support mechanism 231 to the standing position posture.

In a condition in which the control section 66 receives the instruction to transform the support mechanism 231 to the standing position posture, the control section 66 reads information on the height of the (lower) support member in the seated position posture, and, in some cases, information on the angles of the second joint JT2 and the third joint JT3, from the storage section 67.

The control section 66 may control the first joint actuator 245 to move the (lower) support member and change the height of the (lower) support member from the height for the seated position posture to the height for the standing position posture. As a result, the handle 52 shifts up, allowing the vertical position of the handle 52 to be adjusted so as to correspond to the vertical position of the upward shifted hands of the operator O who has changed position from the sitting-on-chair position to the stand-up position. The display section 33 shifts up, too, allowing the vertical position of the display section 33 to be adjusted so as to correspond to the vertical position of the upward shifted eyes of the operator O who has changed position from the sitting-on-chair position to the stand-up position.

In one or more embodiments, the standing position posture and the seated position posture may be changed manually.

Third Embodiment

Figure 13A:
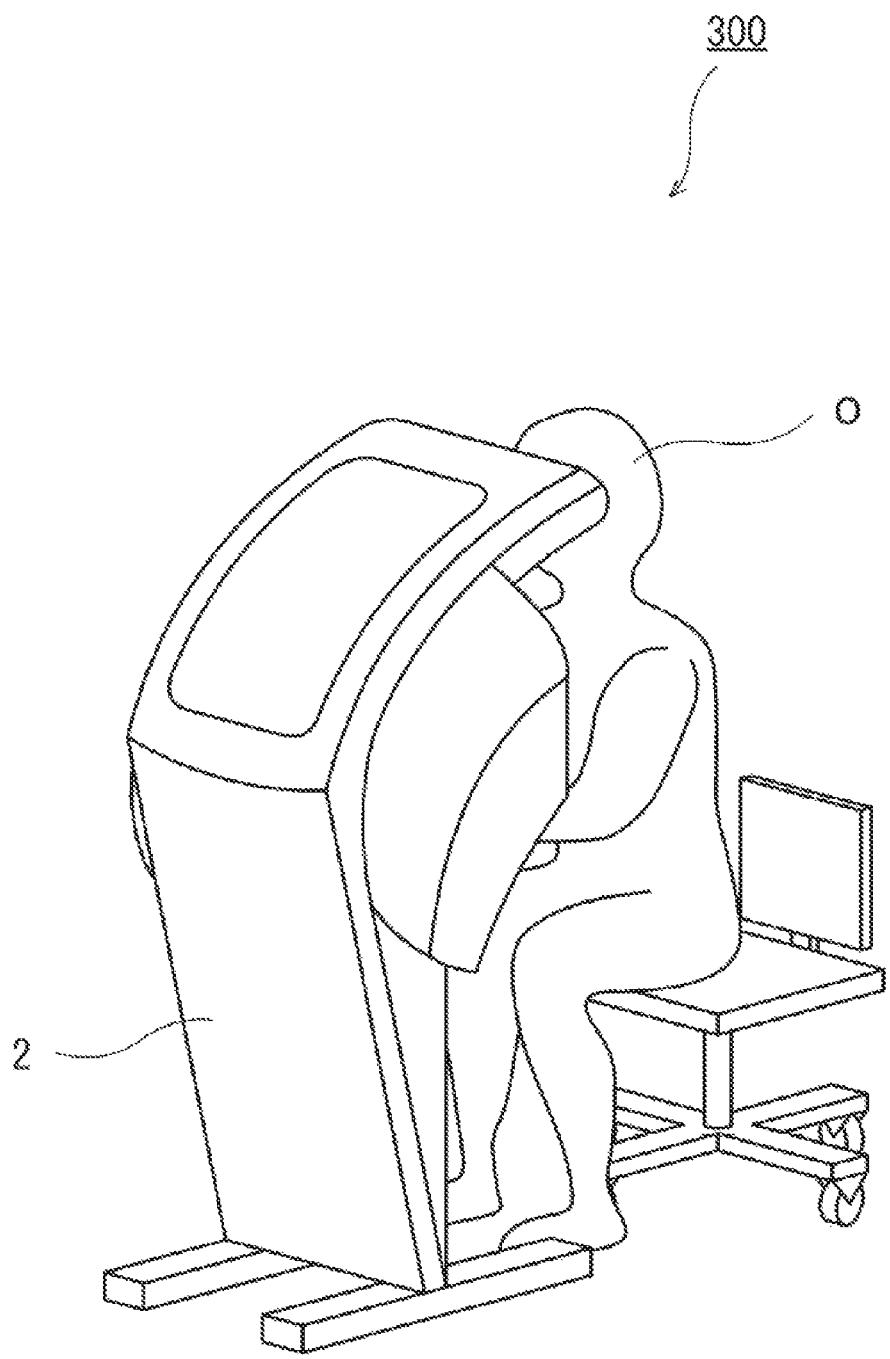
FIG. 13A is a diagram illustrating a perspective view of an example configuration of a remote control apparatus in a seated position posture in a remote surgical system according to in accordance with one or more embodiments.
Figure 13B:
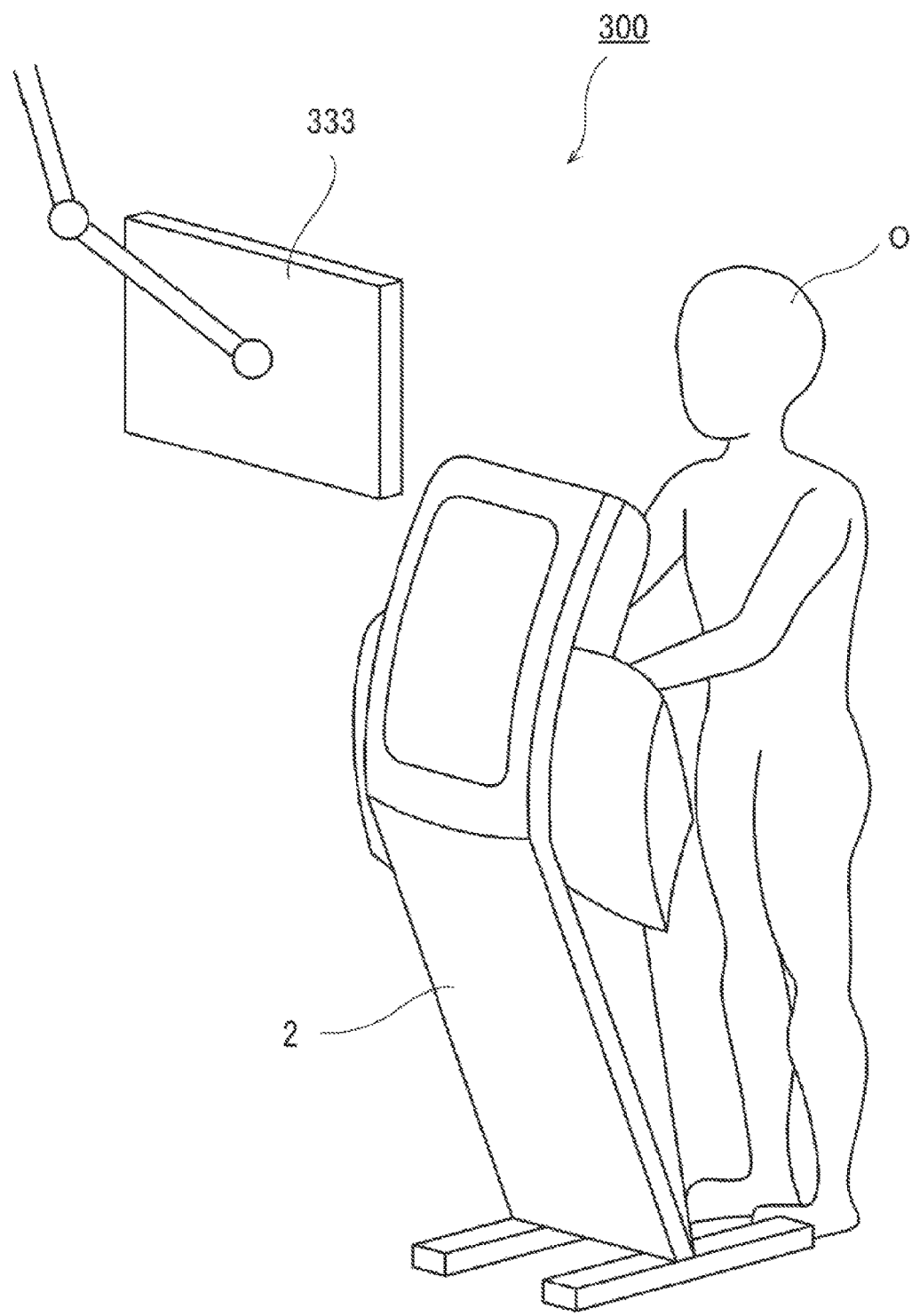
FIG. 13B is a diagram illustrating a perspective view of an example configuration of a remote control apparatus in a standing position posture of a remote surgical system in accordance with one or more embodiments, and an example configuration of an external display device.

FIG. 13A is a perspective view illustrating a remote surgical system 300, wherein the remote control apparatus 2 is in the seated position posture. FIG. 13B is a perspective view illustrating the remote surgical system 300, wherein the remote control apparatus 2 is in the standing position posture.

The remote surgical system 300 in one or more embodiments, may further include an external display device 333 in addition to the patient-side surgery apparatus 1 and the remote control apparatus 2 in the remote surgical system 100, such as is shown in FIG. 1. Such a configuration may allow the operator O to use different display devices depending on whether the operator is in the standing position or the seated position.

The external display device 333 may display the images taken by the endoscope camera probe 13, and may be arranged at a position where the operator O gripping the handle 52 of the remote control apparatus 2 is able to view the image displayed on the external display device 333. For example, the external display device 333 may be attached to the distal end of an arm extending from the ceiling of the operating room, and arranged in the front of the control apparatus 2. The external display device 333 is configured to display the same image as the one on the display section 33.

When the remote control apparatus 2 of the remote surgical system 300 is in the standing position posture, the operator O operating the remote control apparatus 2 can use the handle 52 while viewing the image on the external display device 333, instead of the display section 33.

Figure 14:
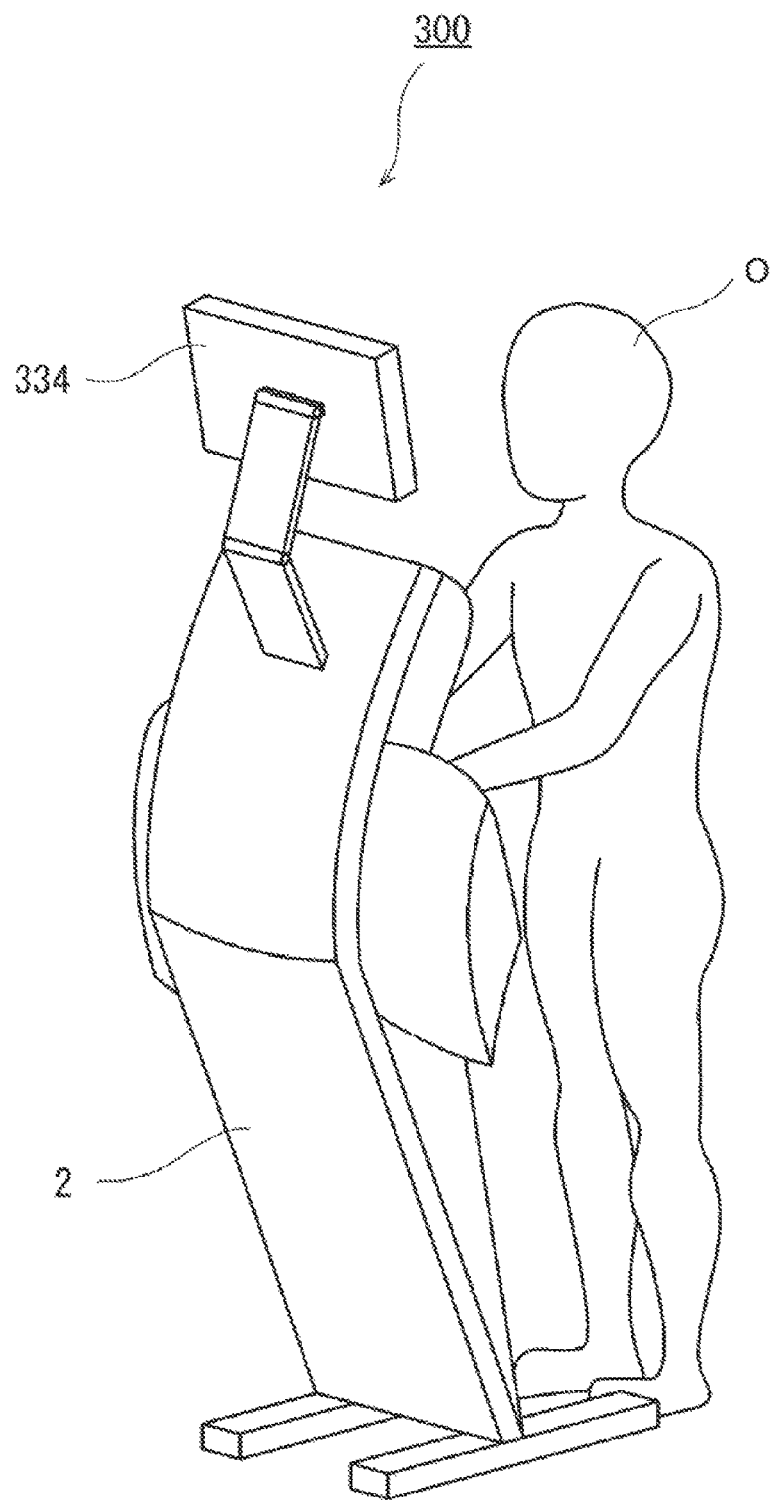
FIG. 14 is a diagram illustrating a perspective view an example configuration of a remote control apparatus in a standing position posture in a remote surgical system according to a variation in accordance with one or more embodiments, which may include an additional display section.

Note that, in some embodiments, the display device suitable for use in the standing position is not necessarily provided as an external device of the remote control apparatus 2. As illustrated in FIG. 14, an additional display section 334, which may be an angle-adjustable display section, may be provided on the body of the remote control apparatus 2 and arranged at a suitable height for the operator O in the standing position to view the images on the display section 334, in addition to the display section 33 arranged at a suitable height for the operator in the seated position to view the images on the display section 33.

In such a configuration, in which the operator O is allowed to use different display devices depending on whether the operator is in the standing position or the seated position, the configuration of the remote control apparatus 2 may be simplified, because the remote control apparatus 2 is suitable to change the vertical position of the handle 5 from the one corresponding to the standing position posture to the one corresponding to the seated position posture, and vice versa. For example, as illustrated in FIGS. 13A and 13B, the second joint JT2 may be omitted. In some cases, the third joint JT3 used to adjust the angle of the display section 33 may also be omitted.

In one or more embodiments, the display section 33 has been described as being arranged at a suitable height for the operator O to view the images. However, this is not intended to exclude a situation in which the operator O performs surgery while viewing the image on the display device 333 or the additional display section 334 as illustrated in FIG. 14 even when the remote control apparatus 2 is in the seated position posture. For example, if the operator O feels tired during surgery, from watching the display section 33 for a long time, the operator O may switch to watching the external display device 333 or the angle-adjusted display section 334 instead of the display section 33, allowing the operator O to perform the surgery in a different position, and hence reduces the fatigue of the operator O.

The remote control apparatuses described in the foregoing embodiments have the first posture suitable for an operator to handle the apparatus in the standing position and the second posture suitable for an operator to handle the apparatus in the seated position. In these remote control apparatuses, the operator may select one of the two postures of the apparatus and adjusts the position before performing surgery, or may change the posture of the apparatus during a long surgery for the purpose of reducing fatigue. In the latter case, if any one of the button 61 for transforming the apparatus to the standing position posture, the button 62 for transforming the apparatus to the seated position posture, or the unlock button 69 is pressed, the operation by the operating handle is invalidated or the control section 66 invalidates the transmission of the movement type instruction to the surgical manipulator, to ensure safety.

In contrast to the disclosed one or more embodiments, the system disclosed in Patent Document 1 and the apparatus disclosed in Patent Document 2 require operators to use the handles either in the standing position or in the seated position, and do not allow the operators to take a position that is desired, or liked. Thus, the one or more disclosed embodiments provide improvements in the operations of remote control apparatuses and relevant systems by enabling the operator to operate a remote control apparatus while taking or changing a position that the operator desires, prefers or likes.

Numerous modifications and alternative embodiments will be apparent to those skilled in the art in light of the foregoing description. Accordingly, this description is to be construed as illustrative only, and has been presented for the purpose of teaching those skilled in the art various embodiments including the best mode for carrying out the invention. The details of the structure and/or function may be varied substantially without departing from the spirit of the invention.

What is claimed is:

1. A remote control apparatus comprising:
   a movable operating handle positioned within an operation area, the movable operating handle inputting a movement type instruction to be executed by a surgical manipulator during a surgery; and
   a support mechanism that supports the operating handle, the support mechanism is configured to transform between a first posture comprising a standing position in which the operating handle is capable of being operated by an operator, and in which the operating handle at a center position of the operation area is positioned at a first vertical position located at a height of 85 centimeters or more from a floor surface such that the operating handle is capable of being positioned close to hands of the operator in the standing position, and a second posture comprising a sitting position in which the operating handle is capable of being operated by the operator, and in which the operating handle is shifted down by 48 centimeters or more from the first vertical position to a second vertical position at which the operating handle at the center position of the operation area is positioned such that the operating handle is capable of being positioned close to the hands of the operator in the sitting position, wherein when an operation of the operating handle results in an input of the movement type instruction during the surgery, one of: the operation of the operating handle; and a transmission of the movement type instruction to the surgical manipulator, while the support mechanism is transformed between the first and second postures, is invalidated.

2. The remote control apparatus of claim 1, wherein in the first posture, the operating handle at the center position of the operation area being configured to be positioned at the first vertical position located at a height of 99 centimeters or more from the floor surface.

3. The remote control apparatus of claim 1, wherein in the second posture, the operating handle being configured to be shifted down by 50 centimeters or more from the first vertical position to the second vertical position.

4. A remote surgical system, comprising:
the remote control apparatus of claim 1; and
a patient-side surgery apparatus having the surgical manipulator being configured to move the surgical manipulator in response to the movement type instruction.

5. The remote control apparatus according to claim 1, wherein:
the support mechanism is further configured to transform between the first posture in which the operation area of the operating handle is included in a clean zone set at or above a predetermined height from a floor surface, and the second posture in which at least part of the operation area of the operating handle is located in a zone below the clean zone.

6. The remote control apparatus of claim 5, wherein the clean zone is set at and above 70 centimeters from the floor surface.

7. The remote control apparatus of claim 5, wherein in the second posture, a vertical position of a lower limit of the operation area of the operating handle is at least 48 centimeters lower than a vertical position of a lower limit of the operation area of the operating handle in the first posture.

8. The remote control apparatus of claim 1, wherein the support mechanism comprises:
a support base;
a lower support whose proximal end is rotatably attached to the support base via a first axis extending in a horizontal direction; and
an upper support whose proximal end is rotatably attached to a distal end of the lower support via a second axis extending in the horizontal direction, wherein
the operating handle is located behind the lower support.

9. The remote control apparatus of claim 8, wherein the lower support is swingably arranged between a standing angle position in which the lower support extends obliquely upward and forward from the support base, and a leaning angle position to which the lower support is rotated forward from the standing angle position, and
the upper support is swingably arranged between a wide angle position in which the upper support extends obliquely upward and backward from the distal end of the lower support at the standing angle position, and a narrow angle position in which the upper support forms an angle with respect to the lower support that is smaller than an angle formed when the upper support is positioned at the wide angle position.

10. The remote control apparatus of claim 8, wherein the first axis and the second axis are approximately parallel to each other.

11. The remote control apparatus of claim 9, wherein in the first posture, the lower support is positioned at the standing angle position and the upper support is positioned at the wide angle position, and
in the second posture, the lower support is positioned at the leaning angle position and the upper support is positioned at the narrow angle position.

12. The remote control apparatus of claim 1, further comprising
a display that displays an image taken by an endoscope camera, wherein
the support mechanism supports the display such that a relative position of the display with respect to the operating handle is changeable in each of the first and second postures.

13. The remote control apparatus of claim 12, wherein the display is rotatably attached around an axis extending in a horizontal direction to the support mechanism.

14. The remote control apparatus of claim 1, further comprising:
a display device that receives an image taken by an endoscope camera and displays the received image, wherein
the display device is provided at a height suitable for the operator to view the image on the display device in the second posture, and an additional display device other than the display device is used in the first posture.

15. The remote control apparatus of claim 14, wherein the additional display device is attached such that an angle thereof is adjustable.

16. A remote surgical system comprising:
the remote control apparatus of claim 14, wherein
the additional display device comprises an external device of the remote control apparatus.

17. A remote control apparatus having a movable operating handle for inputting a movement type instruction to be executed by a surgical manipulator, the remote control apparatus being configured to transform between a first posture capable of enabling an operator in a standing position to operate the remote control apparatus, and a second posture capable of enabling the operator in a seated position to operate the remote control apparatus, the remote control apparatus comprising;
a controller configured to invalidate an operation by the operating handle or a transmission of the movement type instruction while the postures are being changed between the first posture and the second posture.

18. The remote control apparatus of claim 17, wherein, the first posture is the posture in which the operating handle at a center position of an operation area of the operating handle is positioned at a first vertical position located at a height of 85 centimeters or more from a floor surface, and the second posture is the posture in which the operating handle is shifted down by 48 centimeters or more from the first vertical position to a second vertical position at which the operating handle at the center position of the operation area is positioned.

19. The remote control apparatus of claim 17, wherein, the first posture is the posture in which the operation area of the operating handle is included in a clean zone that is set at and above a predetermined height from a floor surface, and the second posture is the posture in which at least part of the operation area of the operating handle is located in a zone below the clean zone.

20. A remote control apparatus comprising:
a movable operating handle positioned within an operation area, the movable operating handle inputting a movement type instruction to be executed by a surgical manipulator; and
a support mechanism that supports the operating handle, the support mechanism is configured to transform between a first posture comprising a standing position in which the operating handle is capable of being operated by an operator, and in which the operating handle at a center position of the operation area is positioned at a first vertical position located at a height of 85 centimeters or more from a floor surface such that the operating handle is capable of being positioned close to hands of the operator in the standing position, and a second posture comprising a sitting position in which the operating handle is capable of being operated by the operator, and in which the operating handle is shifted down by 48 centimeters or more from the first vertical position to a second vertical position at which the operating handle at the center position of the operation area is positioned such that the operating handle is capable of being positioned close to the hands of the operator in the sitting position, and
a position control section including one or more buttons transmit a signal to transform the support mechanism to the first posture and a signal to transform the support mechanism to the second posture, wherein
when an operation of the operating handle results in an input of the movement type instruction during a surgery, one of: the operation of the operating handle; and a transmission of the movement type instruction to the surgical manipulator, while one of the one or more buttons is pressed, is invalidated.

* * * * *